US009851310B2

(12) United States Patent
Aizenberg et al.

(10) Patent No.: US 9,851,310 B2
(45) Date of Patent: Dec. 26, 2017

(54) MANIPULATION OF FLUIDS IN THREE-DIMENSIONAL POROUS PHOTONIC STRUCTURES WITH PATTERNED SURFACE PROPERTIES

(71) Applicant: President and Fellows of Harvard College, Cambridge, MA (US)

(72) Inventors: Joanna Aizenberg, Boston, MA (US); Ian Burgess, Toronto (CA); Lidiya Mishchenko, Cambridge, MA (US); Benjamin Hatton, Toronto (CA); Marko Loncar, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 48 days.

(21) Appl. No.: 15/013,263

(22) Filed: Feb. 2, 2016

(65) Prior Publication Data

US 2016/0282275 A1    Sep. 29, 2016

Related U.S. Application Data

(63) Continuation of application No. 13/990,324, filed as application No. PCT/US2011/061710 on Nov. 21, 2011, now Pat. No. 9,279,771.

(60) Provisional application No. 61/417,779, filed on Nov. 29, 2010.

(51) Int. Cl.
*G01N 21/75* (2006.01)
*G01N 21/78* (2006.01)
*G01N 21/77* (2006.01)
*B82Y 20/00* (2011.01)
*C08G 59/50* (2006.01)
*C08L 63/00* (2006.01)

(52) U.S. Cl.
CPC .............. *G01N 21/78* (2013.01); *B82Y 20/00* (2013.01); *C08G 59/502* (2013.01); *C08L 63/00* (2013.01); *G01N 21/774* (2013.01)

(58) Field of Classification Search
CPC .......... G01N 33/54386; G01N 21/6452; B01L 3/50853; B01L 2300/165; B01L 2300/0858; B01L 2300/0829; B01L 2200/0668
See application file for complete search history.

(56) References Cited

U.S. PATENT DOCUMENTS

2009/0244532 A1*   10/2009   Letant ................... B82Y 20/00
                                                356/244

OTHER PUBLICATIONS

Written Opinion of PCT/US2011/061710, May 29, 2013, pp. 1-8.*

* cited by examiner

*Primary Examiner* — Dennis M White
(74) *Attorney, Agent, or Firm* — Wilmer Cutler Pickering Hale and Dorr LLP

(57) ABSTRACT

A three-dimensional porous photonic structure, whose internal pore surfaces can be provided with desired surface properties in a spatially selective manner with arbitrary patterns, and methods for making the same are described. When exposed to a fluid (e.g., via immersion or wicking), the fluid can selectively penetrate the regions of the structure with compatible surface properties. Broad applications, for example in security, encryption and document authentication, as well as in areas such as simple microfluidics and diagnostics, are anticipated.

40 Claims, 37 Drawing Sheets

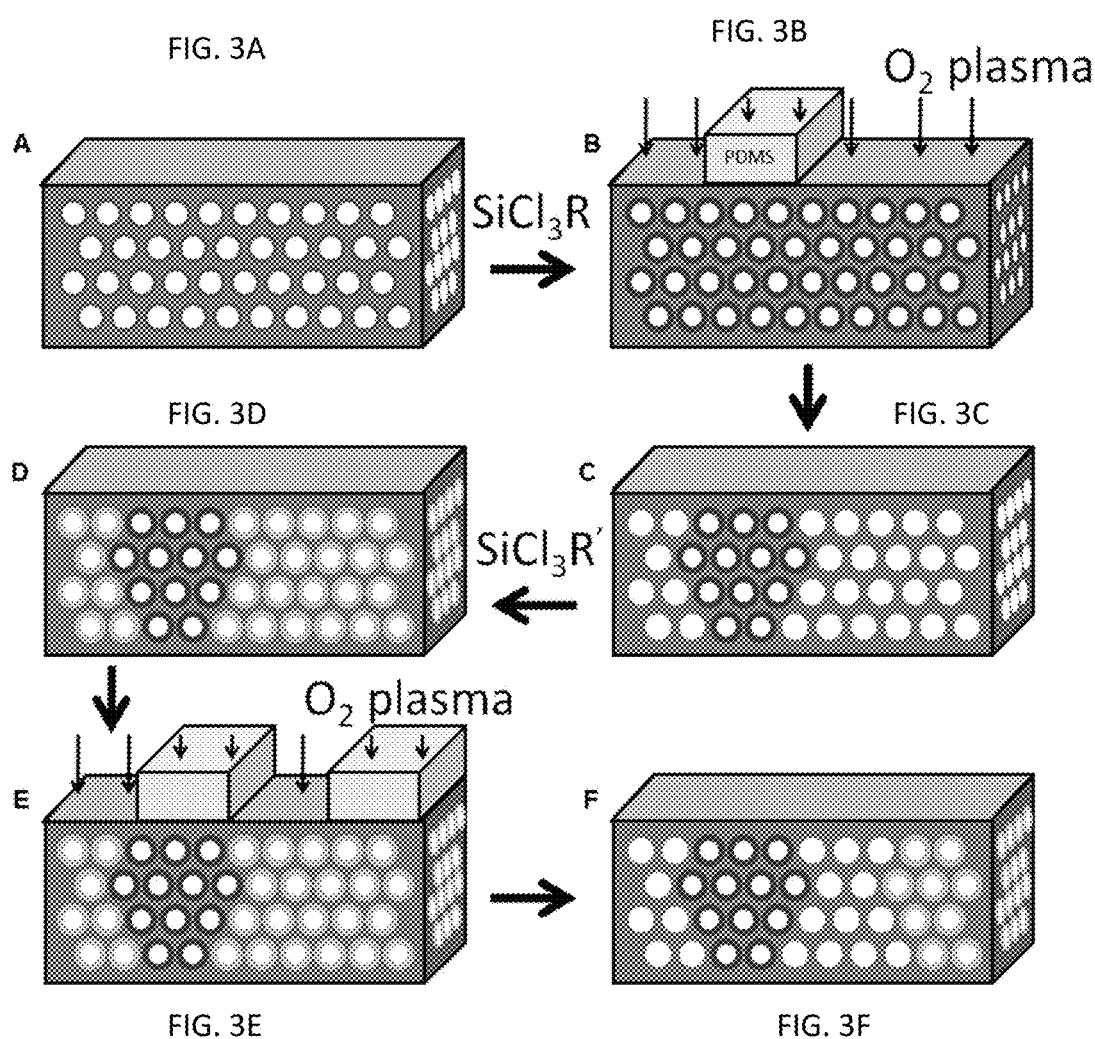

FIG. 12A
FIG. 12B
FIG. 12C
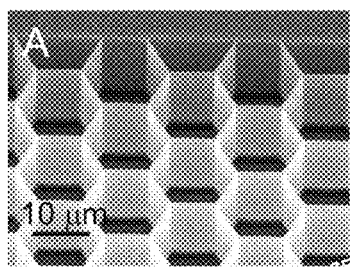
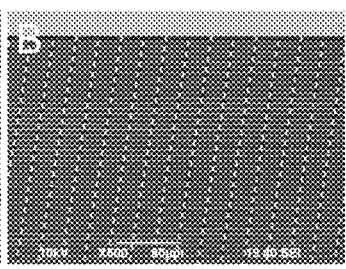
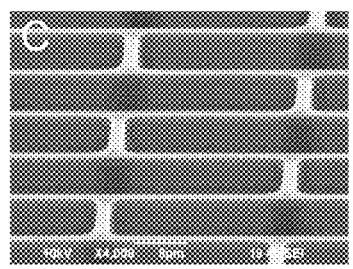
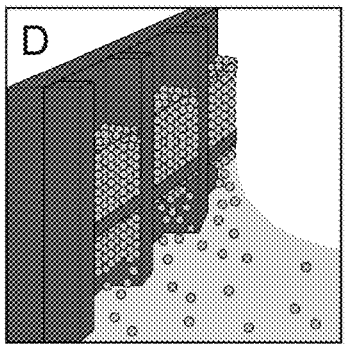
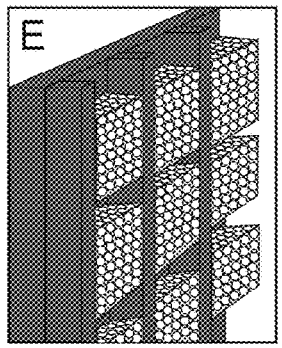
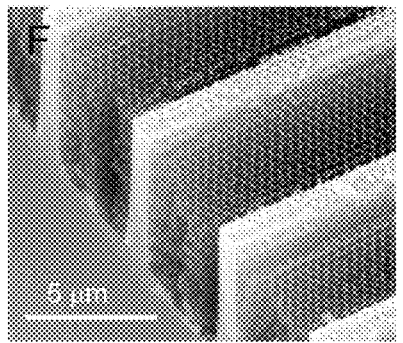
FIG. 12D
FIG. 12E
FIG. 12F FIG. 13A
FIG. 13B
FIG. 13C
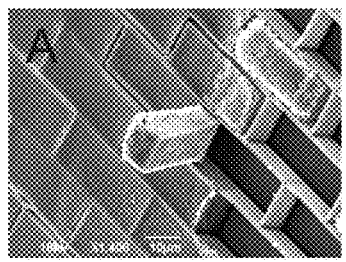 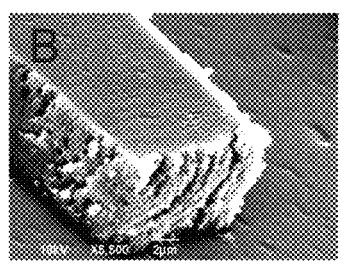 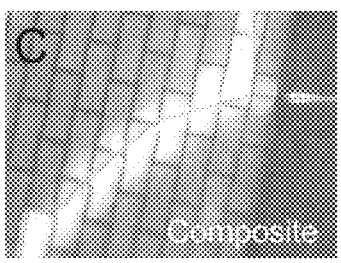
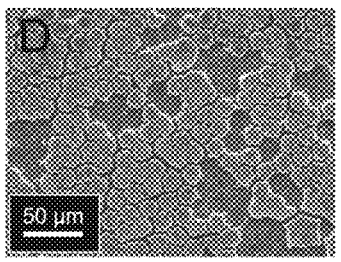 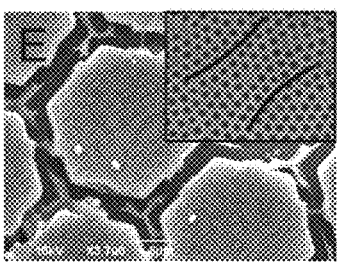 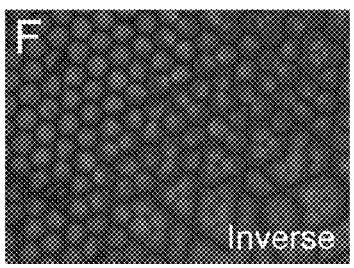
FIG. 13D
FIG. 13E
FIG. 13F FIG. 20A
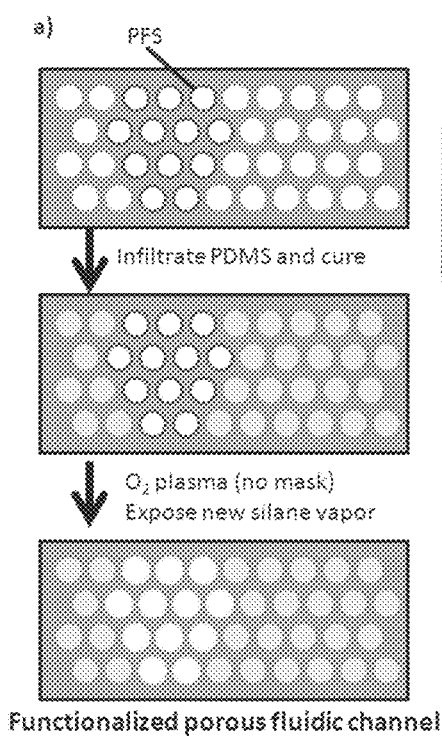
FIG. 20B    FIG. 20C
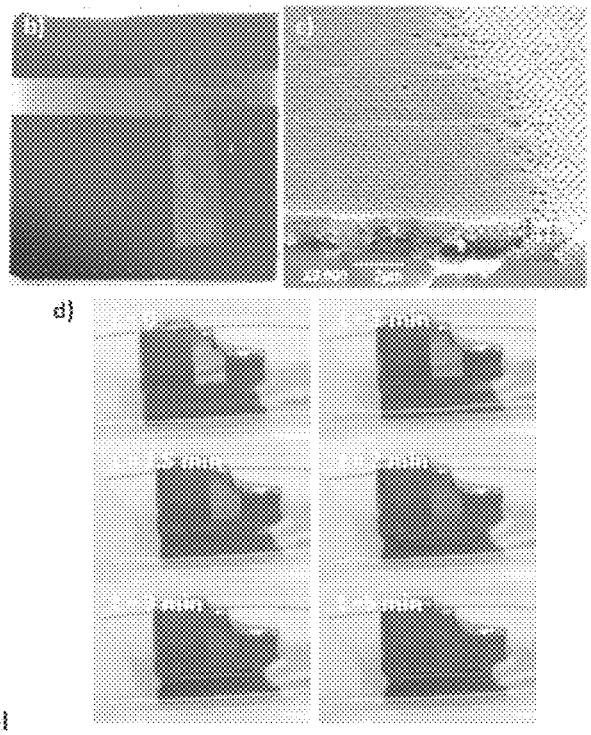
FIG. 20D

FIG. 27

FIG. 28A
FIG. 28B
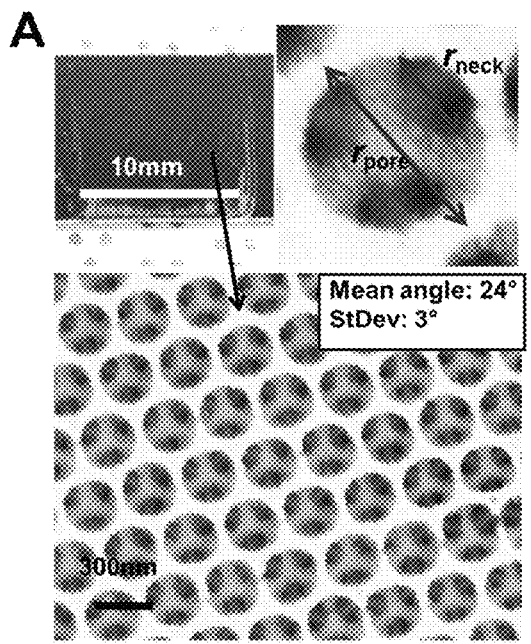
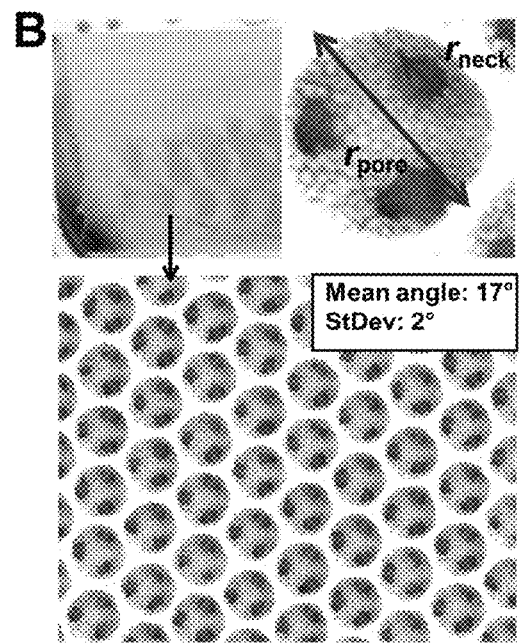

FIG. 31A
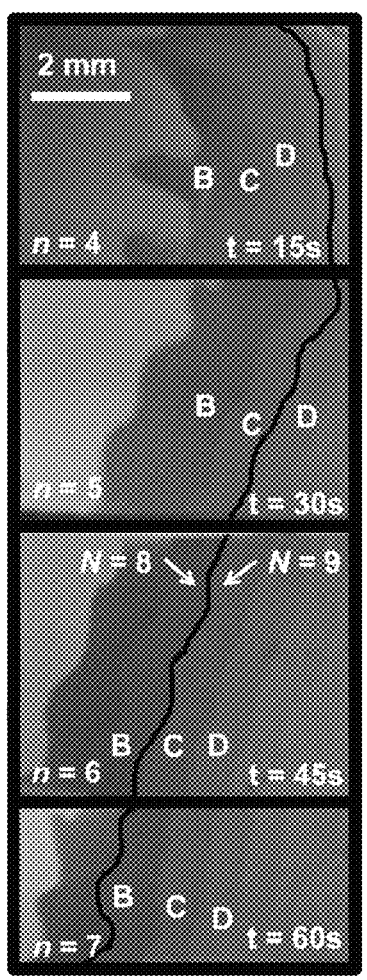
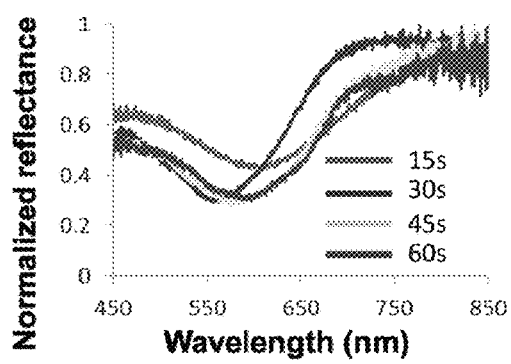
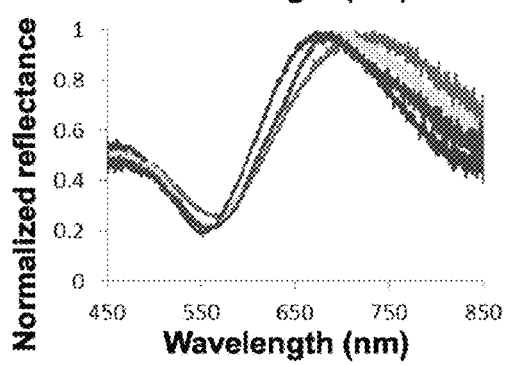
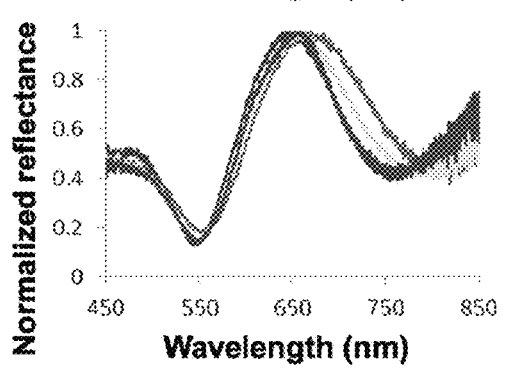

FIG. 33A    FIG. 33B    FIG. 33C
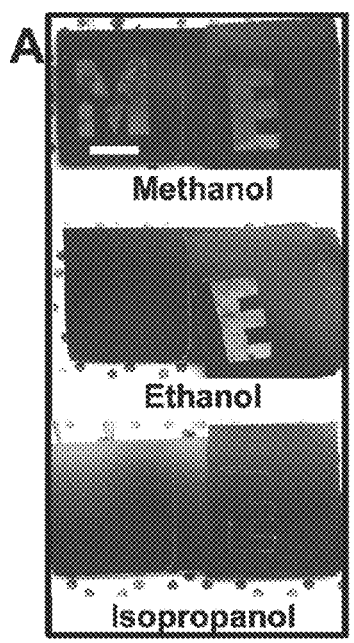
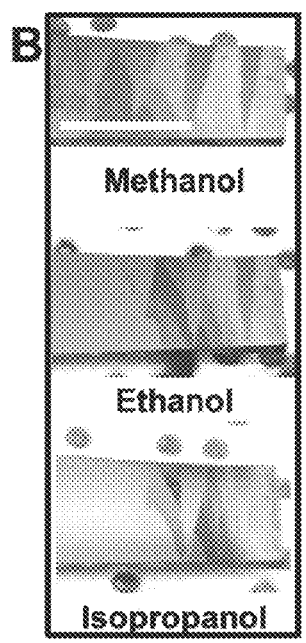
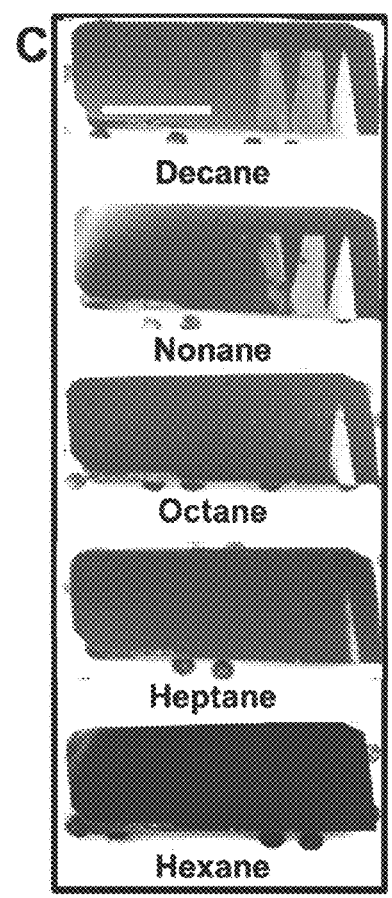
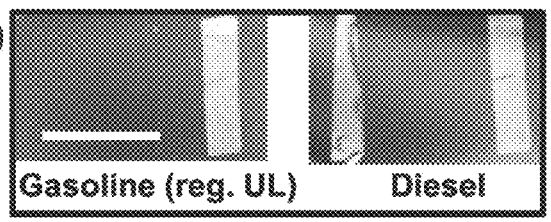
FIG. 33D

MANIPULATION OF FLUIDS IN THREE-DIMENSIONAL POROUS PHOTONIC STRUCTURES WITH PATTERNED SURFACE PROPERTIES

RELATED APPLICATIONS

This application is a continuation application of U.S. application Ser. No. 13/990,324, filed Oct. 2, 2013, which is a national stage application of PCT International Application No. PCT/US2011/061710, filed Nov. 21, 2011, which claims the benefit of the earlier filing date of U.S. Provisional Application No. 61/417,779, filed on Nov. 29, 2010, all of which are hereby incorporated by reference in their entireties.

GOVERNMENT SUPPORT

This work was supported by the United States government under the following grants: Air Force Office of Scientific Research Award FA9550-09-1-0669-DOD35CAP and Department of Energy Award DE-AC05-06OR23100. The government agency has certain rights in this invention.

FIELD OF THE INVENTION

The present disclosure is directed to photonic structures. In particular, the present disclosure is directed to photonic structures that have patterned surface properties that allows preferential interaction with certain fluids.

BACKGROUND

Three dimensional (3D) photonic crystals (PCs), materials with a 3D-periodic variation in refractive index, have been the subject of extensive scientific interest since their inception over two decades ago. Even when there is not sufficient index-contrast to allow a complete 3D photonic bandgap, 3D PCs display exceptionally bright reflected colors arising from photonic stop gaps in particular crystal directions. Structural colors from PC structures are exhibited in a wide range of biological organisms, and often display dynamic tunability. Infiltration and inversion of porous 3D photonic crystals with materials that are capable of dynamic actuation has produced a broad class of PCs with structural colors that can be dynamically manipulated by various forces, such as mechanical force, temperature, electrostatic/electrochemical forces, and the like. However, the surface properties of these porous structures were more or less uniform throughout the photonic crystal.

SUMMARY

In certain embodiments, a product that includes a porous three-dimensional photonic structure having a first region and a second region is described. In certain embodiments, the first region comprises a first surface property on at least some of the interior surfaces of the porous three-dimensional photonic structure; and the first surface property allows a first indicator material to infiltrate at least some of the pores of said first region.

In certain embodiments, the indicator material is a fluid.

In certain embodiments, the first region without the first indicator material has a substantially similar visible appearance to the visible appearance of the second region.

In certain embodiments, the first region includes the first indicator material filled in at least some of the pores of the first region, and the first region has a different reflectance spectrum than the reflectance spectrum of the second region.

In certain embodiments, the first surface property includes wettability, hydrophobicity, hydrophilicity, lyophobicity, or lyophilicity.

In certain embodiments, the second region includes a second surface property on at least some of the interior surface of the porous three-dimensional photonic structure.

In certain embodiments, the second regions comprises a second material which fills the pores of the porous three-dimensional photonic structure.

In certain embodiments, the product further includes a third region which has a third surface property on at least some of the interior surface of the porous three-dimensional photonic structure.

In certain embodiments, the first region comprises a first functional group present on substantially all of the interior surfaces of the first region to provide the first surface property.

In certain embodiments, the first functional group includes reactive groups, protecting groups, hydrophilic groups, hydrophobic groups, lyophilic groups, lyophobic groups, nanoparticles or mixtures thereof.

In certain embodiments, the photonic structure is an inverse opal structure, a mesoporous silica, a short range order structure exhibiting structural color, a quasicrystal, or mixtures thereof.

In certain embodiments, the first region and the second region are patterned to provide an encrypted message that is readily visible after the first indicator material occupies at least some of the pores of said first region.

In certain embodiments, the first region is capable of wicking up the first indicator material.

In certain embodiments, the first region and the second region are located apart from each other in a lateral dimension of the photonic crystal.

In certain embodiments, the first region and the second region are located apart from each other in a vertical dimension of the photonic crystal.

In certain embodiments, the pore sizes are selected to provide a predetermined energy barrier for the first indicator material to infiltrate at least some of the pores of said first region.

In certain embodiments, the photonic crystal further includes one or more additives within the photonic crystal to enhance optical response of the photonic crystal.

In certain embodiments, the first indicator material includes a mixture of different fluids.

In certain embodiments, different devices, such as a sensor, encryption device, and the like can be fabricated.

In certain embodiments, a method including the following steps is described: providing a porous three-dimensional photonic structure; and patterning a first region of said porous three-dimensional photonic structure with a first surface property on at least some of the interior surfaces of the porous three-dimensional photonic structure; where the first surface property allows a first indicator material to occupy at least some of the pores of said first region.

In certain embodiments, the method further includes providing a mask in or over at least a second region of said porous three-dimensional photonic structure.

In certain embodiments, the first region includes a first functional group present on substantially all of the interior surfaces of the first region to provide the first surface property.

In certain embodiments, the first functional group includes reactive groups, protecting groups, hydrophilic groups, hydrophobic groups, lyophilic groups, lyophobic groups, nanoparticles or mixtures thereof.

In certain embodiments, the method further includes: providing said first region of said porous three-dimensional photonic structure with a second surface property by providing a reagent that reacts with said first functional group.

In certain embodiments, the first surface property includes wettability, hydrophobicity, hydrophilicity, lyophobicity, or lyophilicity.

In certain embodiments, the method further includes: providing said first indicator material that selectively fills at least some of the pores of said first region.

In certain embodiments, the first indicator material wicks into at least some of the pores of the first region.

In certain embodiments, the first region is patterned to provide an encrypted message that is not visible until the first indicator material occupies at least some of the pores of the first region.

In certain embodiments, the method further includes: patterning a second region of said porous three-dimensional photonic structure with a second surface property on at least some of the interior surfaces of the porous three-dimensional photonic structure.

In certain embodiments, the photonic structure is an inverse opal structure, a mesoporous silica, a short range order structure exhibiting structural color, a quasicrystal, or mixtures thereof.

BRIEF DESCRIPTION OF THE DRAWING

FIG. 3 A-F shows a schematic diagram of selectively modifying the surface properties of a porous three-dimensional photonic structure with three different functional groups in accordance with certain embodiments;

FIG. 12A-F shows a schematic and SEM images of different microstructures that can be utilized to form photonic crystal particles in accordance with certain embodiments;

FIG. 13A-F shows SEM images of some exemplary photonic crystal particles formed in accordance with certain embodiments;

FIG. 20A-D shows a "visible" microfluidic channel formed by selectively filling a functionalized three-dimensional photonic crystal with a solid precursor and wicking fluid through the structure in accordance with certain embodiments;

FIG. 27 shows different selectivity of photonic crystals functionalized with two different vertical gradients of functional groups for 90% ethanol and decane in accordance with certain embodiments;

FIG. 28A-B shows SEM images of inverse opal photonic crystals having different neck diameters in accordance with certain embodiments;

FIG. 31A-D shows images and reflectance spectra of photonic crystal having a vertical gradient of functional groups at different thicknesses that exhibits different optical properties depending on the depth of infiltration for the same infiltrating liquid in accordance with certain embodiments;

FIG. 33A-D shows images of different photonic crystals exhibiting different types of liquid selectivity in accordance with certain embodiments.

DETAILED DESCRIPTION

A photonic structure having patterned surface properties that allows preferential interaction with certain selected fluids and reagents are described. Such a material can be used to embed desired information through selective wetting of the photonic structure.

In certain embodiments, 3D porous photonic structures patterned with regions of different functional groups that have differential wetting of liquids properties, and a method for producing such a structure by selective addition or removal of functional groups is described. The liquid wetting can cause a visible color change due to a change in effective index contrast.

Generally, a three-dimensional structure having a periodic pattern of higher index refractive material and a lower refractive index material, such as air, can be utilized as a photonic structure. The photonic structure can be tuned to have a size scale and refractive index contrast so that structural colors arise near the visible wavelengths. Generally, to obtain structural colors nears the visible wavelengths, photonic structures having nanometer to micron-scale feature sizes are desired.

As used herein, photonic structures can include structures having long range order (e.g., single crystal photonic crystals, single crystal mesoporous structures, etc.), structures having medium range order (e.g., photonic crystals having many small crystalline domains, mesoporous structures having many small crystalline domains, quasicrystals, etc.) and even short range order (e.g., glasses that have a fixed pore sizes, etc.). In certain embodiments, the photonic structure can provide a structural color. In some other embodiments, the photonic structures can provide change in appearance due to interference effects. Generally, photonic structures are meant to encompass structures that can provide optical effects in the visible wavelengths.

Particularly, when porous photonic structures are involved (e.g., pores having sizes on the order of about tens to hundreds of nanometers, pores in the mesoscale size ranges, etc.), it was conventionally thought that selective or patterned functionalization of the photonic structures would be difficult or nearly impossible as diffusion of etchants or reagents through the pores were likely to occur, washing out spatial contrast in surface properties. Nevertheless, contrary to conventional wisdom, the present disclosure provides photonic structures having patterned surface properties and methods for making such structures.

Formation of a Photonic Crystal

Figure 1:
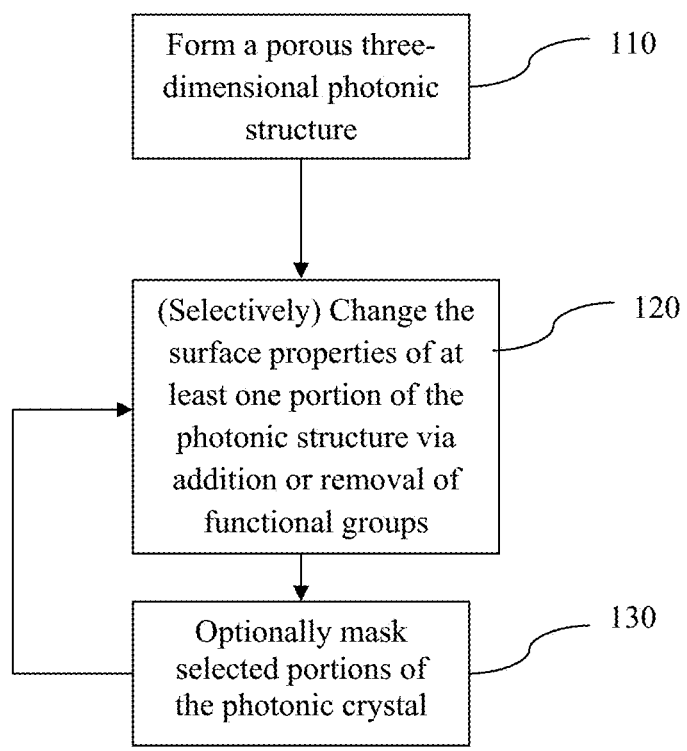
FIG. 1 shows a schematic illustrating a method for selectively changing the surface properties of a porous three-dimensional photonic structure in accordance with certain embodiments.

As shown in FIG. 1, a photonic structure can first be formed (see step 110). While any porous three-dimensional (3D) photonic structures can be utilized, a widely utilized photonic structure that provides visible wavelengths structural color and interconnected porosity involve use of inverse opal structures.

Any suitable 3D, porous photonic structure material can be utilized. In certain embodiments, a porous three-dimensional photonic structure can be utilized, where the photonic structure has at least one higher refractive index material phase and a plurality of pores as the lower refractive index material phase that are interconnected with each other. In certain embodiments, the high refractive index material phase can also contain a plurality of pores that are smaller than the pores forming the low refractive index material. In certain embodiments, pores can have aperiodic arrangement, exhibiting incoherent scattering that can be tuned by selective liquid infiltration. In certain embodiments, a plurality of different high refractive index materials can be utilized to form the higher refractive index material phase. In certain embodiments, a plurality of different high, medium, and low refractive index material phases may be present.

Suitable exemplary porous three-dimensional photonic structures include $SiO_2$ based inverse opals structures. As a non-limiting example, large-area single-crystal inverse opal photonic crystals can be prepared by evaporation-induced coassembly of a monodisperse colloidal suspension of particles (e.g., poly (methyl methacrylate) (PMMA) nanospheres (d~280 nm)) with a silica sol-gel solution (e.g., prepared from the acid-catalyzed hydrolysis of tetraethyl orthosilicate (TEOS)) onto a substrate. Thereafter, the colloidal template particles can be removed (e.g., by calcination for 8 h at 500° C.). The resulting porous inverse-opal photonic crystals generally have a face-centered-cubic geometry. Such a technique is described in PCT/US09/55044, which is incorporated by reference herein in its entirety.

Alternative techniques exist to make any desired three-dimensional photonic structure, as would be readily apparent to one of ordinary skill in the art. Other techniques include sequential formation of a colloidal template followed by infiltration, polymerization induced by interference patterns produced by laser, direct laser writing (e.g. by two-photon polymerization), glancing-angle deposition, stacking of 2D photonic structures by micromanipulation, etc. Selection of how and what photonic structure to form will be dependent on the ease of fabrication, desired photonic or stop bandgap, desired degree of long range order, and the like. For example, if a long range order is desired, co-assembly technique described above may be favored over the sequential formation of a colloidal template followed by infiltration because unlike post-infiltrated colloidal inverse opals, photonic structures formed via the above-mentioned co-assembly technique can provide a near single-orientation structure with the (110) direction pointed in the growth direction.

In certain embodiments, suitable three-dimensional photonic structure materials can selectively be provided with desired surface properties. Desired surface properties include wettability, hydrophobicity, hydrophilicity, lyophilicity, lyophobicity, and the like.

Desired surface properties can be provided in any number of techniques, including functionalization by formation self-assembled organic monolayers (SAMs) on the surfaces of the porous structure, functionalization by etching away materials on the surface of the porous structure, deprotection or protection of moieties present on the surface of the porous structure, reaction of molecules carrying desired functional groups with reactive groups on the surface of the porous structure, attachment of nanoparticles, and the like. Generally, "functional group" is meant to encompass any specific surface property, and "functionalized photonic structure" is meant to encompass a porous structure having desired surface properties, whether through additional pendant groups or through reaction or etching away of existing moieties on the surface of the pores, or through surface adsorption.

For example, inverse opal $SiO_2$ can be selectively surface-functionalized when exposed to alkylchlorosilanes in solution or in the vapor phase, a class of compounds which are widely commercially available. The chlorosilane moiety can react with an exposed polar surface group of the inverse opal $SiO_2$ walls, replacing it with the organic group attached to the chlorosilane. In certain embodiments, the native surface groups of the photonic materials can also be used with or without modification as an end-functionality.

Functionalization of the Photonic Crystal

Returning to FIG. 1, at least one portion of the photonic structure is functionalized with desired functional groups (see step 120). In certain embodiments, the entire or multiple portions or a single portion of the photonic crystal can be functionalized with desired functional groups. Suitable functional groups include organic groups, polar groups, hydrophilic groups, hydrophobic groups, metal-binding groups, biological surface-binding groups (e.g. anitbodies, biotin, DNA etc.), nanoparticles and the like.

In certain embodiments, the functional groups may be chosen based on particular affinity to certain materials, such as specific solvents, vapors, chemical reagents, biological reagents, metals, nanoparticles, and the like.

In certain embodiments, the functional groups can be chosen based on particular repulsion to certain materials, such as specific solvents, vapors, chemical reagents, biological reagents, metals, nanoparticles, and the like.

In certain embodiments, the functional groups can be chosen based on reactivity of the functional groups (with the fluid itself or something suspended in the fluid). In certain embodiments, the functional groups may be non-reactive while in other embodiments, the functional groups may be reactive.

In certain embodiments, desired functional groups can be provided through a number of different techniques. Suitable techniques include cleaving off certain protecting groups using etchants, reactants, radiation, plasma and the like, and/or exposing desired functional groups.

Other suitable techniques involve reaction of reactive functional groups with other introduced functional moieties to provide new desired functional groups. In certain embodiments, the reactive functional groups can be obtained after cleaving off certain protecting groups, as described above, from the surfaces of the porous three-dimensional photonic structures, and via subsequent exposure of these newly-formed functional groups of the porous three-dimensional photonic structures to reactive groups, and the like.

Other techniques involve formation of a self-assembled monolayer on the surface of the porous three-dimensional photonic structure through covalent, ionic, or van der Waals interactions with the surface, possibly following the "cleaving" step above. Other functionalities can also be added through grafting of additional compounds/molecules to a self-assembled monolayer, or adsorbing or growing materials on top of a self-assembled monolayer. New surface functionality can also be achieved by adsorption of mixed layers of two or more species.

Patterning to Obtain Functionalized Photonic Crystal

In step 130, selected areas of the photonic structure can be masked. A suitable mask can include any material (e.g., rubbery) that can provide a good seal to the surface of the photonic structure with or without the application of pressure. Moreover, the suitable mask should also be easily removed from the photonic structure surface. Exemplary masking materials form good contact with the photonic structure surface so that the underlying regions are fully shielded during the exposure process. In some instances, the mask can be clamped or secured to the surface using external forces to ensure full and sealing contact with the photonic crystal. In addition, they are of sufficient material integrity that do not flow or change shape upon exposure to etching medium, which can result in the undesired infiltration of the porous network of the photonic structure. Suitable masks include, for example, polydimethylsiloxane, polyurethane, and the like.

In some embodiments, step 130 can also be carried out using a mask deposited from fluid (e.g. spin-on polymers, photoresist, etc.) when the surface chemistry of the photonic structure is first adjusted so as to resist infiltration of the liquid/solvent. Alternatively, to allow for nanoscale feature patterning the photonic structure could be infiltrated first with a selectively etchable material (e.g. photoresist). After the material is selectively patterned and removed in certain areas, the surfaces chemistry of the newly-exposed photonic structure can be modified according to step 120. Subsequently, the remaining material (e.g. photoresist) could also be removed.

Thereafter, steps 120 and 130 can be repeated as many times as desired.

Many different embodiments can be envisioned. For example, step 120 can involve a multi-step process where the desired functional groups are provided through multiple etching, reaction, dissolution, and the like.

In certain embodiments, the photonic structure may already be provided with suitable functional groups and step 130 may be carried out before 120.

Embodiment 1

Lateral Patterning of Different Functional Groups

In certain embodiments, one or more regions of the photonic structure can be selectively provided with reactive functional groups (e.g., hydroxyl, amine, aldehyde, carboxylic acid, sulfonic acid, thiol, nitrile, isothiosulfate, enzyme, antibodies, DNA, RNA, and the like). For example, by masking one or more desired regions of the photonic structure (i.e., carrying out step 130) and exposing the unmasked portions to reagents or etchants (e.g., oxygen plasma, radiation, reactive ions, reactive chemical species, and the like), reactive functional groups can be formed.

Thereafter, in certain embodiments, subsequent reactions can be carried out with the reactive functional groups to provide additional, functional groups. For example, vapors or solutions of certain reactants (e.g., different alkylchlorosilane, organosilane, organothiol, DNA, antibodies, and the like) can be introduced, allowing the reactants to be grafted onto the reactive functional groups.

In certain embodiments, the reactive functional groups that remain after etching/exposure to reactive groups can themselves be used without further reactions in desired applications. Furthermore, the native surface chemistry of the photonic crystal material can be used with or without modification as a functionality in the final product.

In certain embodiments, different regions can be provided with identical functional groups. However, depending upon the density or amount of functional groups present on the porous surface, different fluids may be attracted to the respective regions having different density or amount of the functional groups. For example, a first region having 100% coverage of hydrophobic functional group may entirely repel alcohol mixed with water whereas a second having 10% coverage of hydrophobic functional group may attract the same alcohol mixed with water.

In certain embodiments, the functional groups can provide a desired level of "contrast" between the type of materials the functional groups are attracted to or repulsed by. "Contrast," as used herein, refers to the degree of differentiation the respective regions with desired surface properties can make with respect to similar fluids. In certain embodiments, regions having a high contrast may be able to differentiate between two liquids that contain mixtures of very chemically similar fluids, such as alcohols containing differing amounts of water. An exemplary photonic crystal having regions of high contrast may be able to differentiate between a first mixture containing 95% ethanol and 5% water from a second mixture containing 90% ethanol and 10% water. In other embodiments, regions having a low contrast may be able to differentiate between two liquids that contain mixtures of very chemically different fluids, such as organic solvents and alcohols.

In certain embodiments, the differing regions can be patterned with different degrees of lateral resolution. For example, if small microscopic patterns are desired, the various regions can be provided with a high resolution where the boundary between the regions having different surface properties can be sharp. In some other embodiments, where a gradual shift is desired, the differing regions can be patterned so that the boundary between the regions gradually changes in the lateral direction.

In certain embodiments, the order in which the different functional groups are added can be optimized to produce different global surface properties in the channels of photonic structure. For example, it is observed that differences in wetting properties and contrast between areas of different functionality are achieved depending on whether the functional groups are added starting with the largest surface groups and ending with the smallest groups or in the reverse order. For example, if molecules having long and bulky functional groups are first added, there may be sufficient space in between the attached functional groups to allow further addition of molecules having smaller functional groups. In contrast, if molecules having short and compact functional groups are first added, the molecules may be too compactly added onto the surface and not allow further addition of molecules having larger functional groups. As another example, if small molecules are first added and contain large number of defect sites that allow addition of molecules having large functional groups, insertion of those larger functional groups may have a significant impact on the overall properties as the later added larger functional groups may mask the functional groups of the earlier added smaller molecules.

In certain embodiments, the functional groups can also be selectively modified or even completely removed, exposing the native surface chemistry (e.g. SiOH for silica) through longtime exposure to reactants or etchants (e.g., $O_2$-plasma, piranha cleaning solution, radiation, reactive ions, etc.), allowing the photonic structure to be recycled and provided with new patterns of different functional groups. Additionally, incomplete removal of a functional group, with or without subsequent application of step 120 to graft a new functionality to what remains, can be used to create new surface functionalities.

In certain embodiments, the functional groups may be completely removed, by for example, flood exposure of the structure to an etching agent. Thereafter, steps 120 and 130 can be repeated as described the above with arbitrarily different masks and functional groups, making the photonic structures fully re-writable.

As noted above, it was conventionally thought that selective or patterned functionalization of inner surfaces of porous three-dimensional photonic structures would be difficult or nearly impossible when utilizing air as the low refractive material as diffusion of etchants or reagents through the pores were likely to occur. Nevertheless, contrary to conventional wisdom, by carefully controlling the etching and/or deposition conditions as described herein, the present disclosure provides photonic structures having patterned surface functional groups and methods for making such structures.

Figure 2:
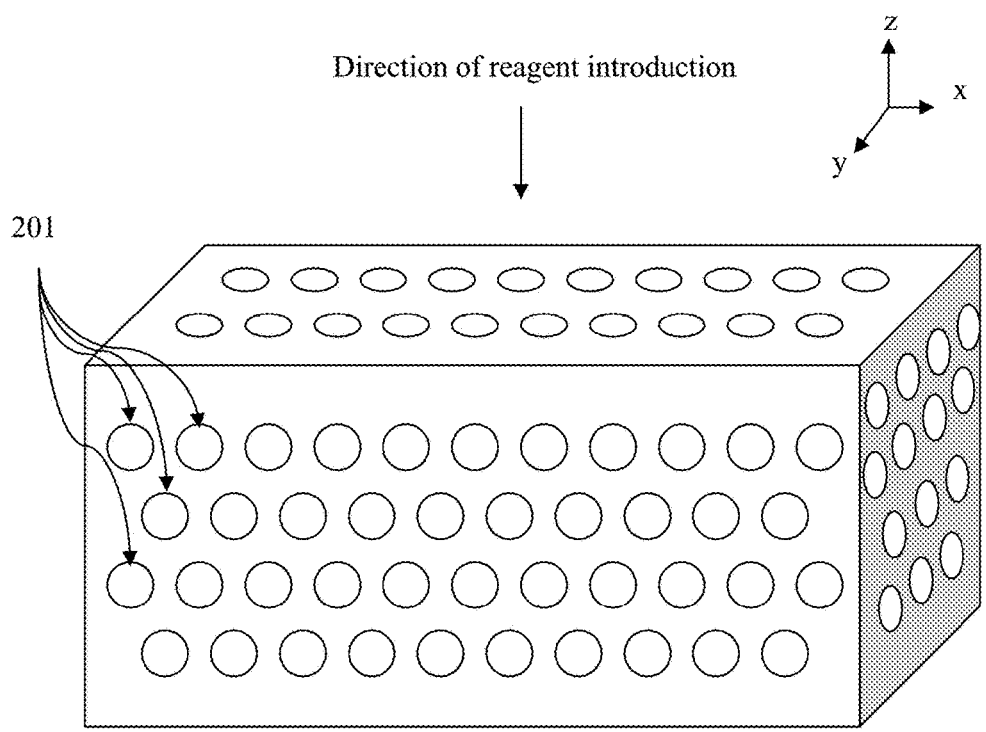
FIG. 2 shows a porous three-dimensional photonic structure where reagents are introduced to locally change the surface properties of the photonic structure in accordance with certain embodiments.

Without wishing to be bound by theory, reagents and or conditions (e.g., chemicals, plasma power, UV power, etc.) can be selected so that the vertical diffusion (e.g., along the z-axis direction in FIG. 2) of the reagents through the porous medium is the same or faster than the lateral diffusion of the reagents through the porous medium (e.g., along the x- and y-axes in FIG. 2) inside the photonic structure. However, some lateral diffusion is desirable because without any lateral diffusion, sufficient functionalization may not occur throughout the photonic structure (e.g., preventing functionalization of the top regions 201 of the pores) due to shadowing effects. Hence, a vertical diffusion to lateral diffusion ratio on the order of magnitude of 1 to 1 or greater may be desired to achieve the optimal amount of functionalization throughout the pore surfaces. In general, one would expect the lateral resolution of a given patterning process to be roughly the product of the structure thickness and the lateral-to-vertical diffusion ratio.

In certain embodiments, lateral and vertical diffusion for the particular porous three-dimensional photonic structure is controlled so that the functional groups are distributed uniformly on substantially all of the interior surfaces of desired regions of the photonic structures.

In some other embodiments, lateral and vertical diffusion for the particular porous three-dimensional photonic structure is controlled so that the functional groups are located on certain sides of the pores (e.g., bottom portion, etc.).

One non-limiting surface patterning technique is illustrated in FIG. 3. As shown, an inverse opal silica photonic crystal is utilized (see FIG. 3A).

The entire structure is functionalized by exposure to vapors of a functional group (e.g., chlorosilane with an attached organic functional group, R). Particularly, the inner pore-surfaces of the photonic crystal (PC) (e.g., $SiO_2$) can be functionalized by exposure to a molecule containing a desired functional group (e.g., an alkyl chlorosilane with a non-wetting organic group, $SiCl_3R$) to obtain the structure shown in FIG. 3B.

Exposure to an etchant (e.g., oxygen plasma) through a removable mask (e.g., PDMS slabs sealed to the surface under pressure, such as a clamp, that can be readily peeled off after etching without damaging the structure) can selectively modify the surface only in the unprotected regions. For example, oxygen plasma can etch organic functional groups and add polar oxygen species (e.g., ROH, RCOOH, RCOH etc., referred to hereafter collectively as ROH for simplicity) to the surface. The resulting structure is shown in FIG. 3C. ROH groups can be added on the bare silica surface or to the ends of partially etched organic monolayers. The plasma-treated ROH surfaces can be utilized as wetting surfaces for contrast and also as surfaces with greater affinity for chemisorption of subsequent alkylchlorosilanes.

Exposing the now patterned structure to vapors of a second functional group containing material (e.g., second alkyl chlorosilane, $SiCl_3R'$) adds a new functional group to surface sites that are occupied by these reactive oxygen species and not already occupied by a non-reactive organic group (e.g. in areas protected by the mask in the previous step). As shown in FIG. 3D the surface is exposed to, a second alkylchlorosilane with a less hydrophobic organic group, R', to impart different wettability to the plasma-treated surfaces.

Further plasma-etching through another mask with a different pattern (see FIG. 3E) can produce a pattern that is now composed of three different surface functional groups, including ROH, as shown in FIG. 3F.

This process represents an example of steps 120 and 130 which can be repeated n times to produce (n+1) different surface chemistries. Different chemistries are applied by adding new chlorosilanes or adjusting the etching or chlorosilane exposure conditions to produce mixed monolayers or monolayers containing grafted organic groups originating from different chlorosilanes.

An inverse opal structure can be recycled and re-written through flood exposure of the structure to oxygen plasma for long time, removing organic monolayers and restoring a polar functional group throughout the structure. The above procedure can then be repeated with arbitrarily different masks and functional groups.

Figures 4A, 4B, 4C:
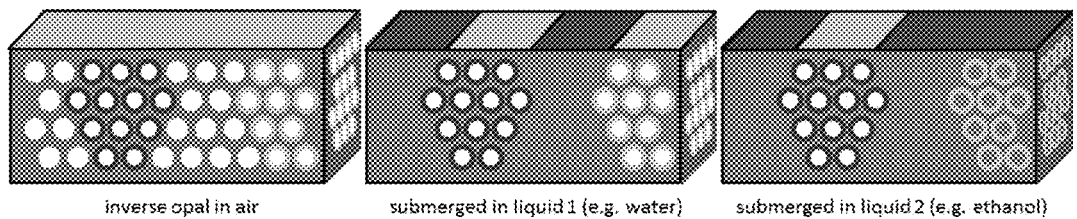
FIG. 4 A-C shows a schematic diagram selective infiltration of different liquids into different regions of a selectively functionalized photonic structure in accordance with certain embodiments.

FIG. 4 shows a schematic indicating the selective infiltration of different solvents into the areas of different functional groups and their resulting color changes for the structure described above. The difference in refractive index contrast between un-infiltrated (e.g., $n_{PC}/n_{air} \sim 1.5/1.0$) and infiltrated (e.g., $n_{PC}/n_{liquid} \sim 1.5/(1.3$ to $1.4))$ regions produces a visible color contrast in the structure. In certain embodiments, if the infiltrating liquid provides a refractive index match with the photonic crystal (e.g., both $n_{PC}$ and $n_{liquid} \sim 1.5$), filling of the photonic crystal can lead to a transparent material while the un-infiltrated region continues to exhibit color. While most solvents penetrate the ROH-functionalized regions, the infiltration of solvents into the two hydrophobic regions (see FIG. 4) may depend on the surface tension of the solvent. If these two regions have different degrees of lyo- or solvo-phobicities, there will exist solvents that penetrate the pores of the less lyophobic region while not penetrating the pores of the more lyophobic regions. For example, high-surface-tension liquids such as water may only penetrate ROH regions, generating two different possible patterns observed (depicted by the color of the top surface in the diagram). If this procedure is repeated n times to produce a photonic crystal with regions of n lyophobic regions with different lyophobicities on an ROH-background, one can find at least n liquids, in each of which a different pattern is observed from combinations of infiltrated and uninfiltrated hydrophobic regions. The uninfiltrated regions can carry the original photonic color, while the infiltrated regions can appear darker and provide a significant contrast compared to the bright appearance of the uninfiltrated region.

Embodiment 2

Enhancing Optical Response of Photonic Crystals

Figure 5:
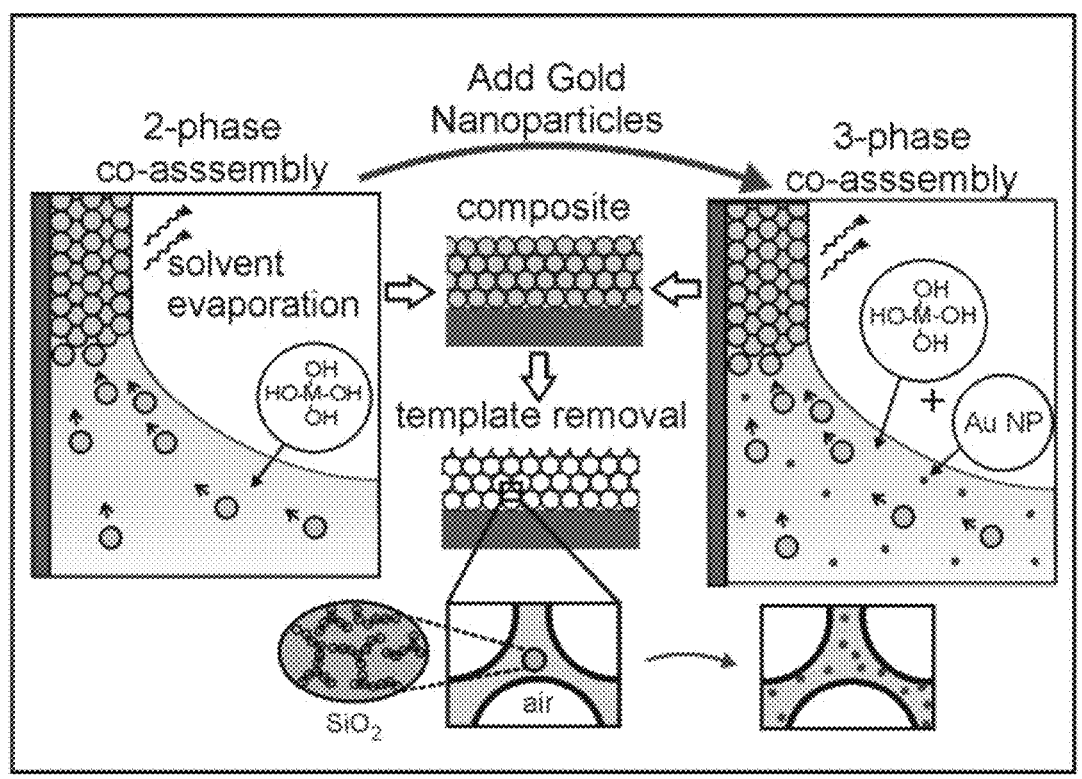
FIG. 5 shows a schematic diagram incorporating gold nanoparticles into the photonic crystal in accordance with certain embodiments.

In certain embodiments, additional materials that enhance the optical response (e.g., enhance color contrast) can be incorporated into the photonic crystal. For example, nanoparticles (e.g., gold nanoparticles, silver nanoparticles, carbon-black nanoparticles, quantum dots, dyes) can be incorporated into the non-porous regions of the photonic crystal during growth, which in turn may enhance the optical response of the photonic crystal (see FIG. 5). FIG. 5 illustrates in the left-hand schematic the two-phase assembly of a photonic crystal from a colloidal suspension of a templating particle and a precursor (e.g., silica precursor). A support is slowly drawn from the mixture and a composite layer of the templating particles surrounded by the precursor is formed as solvent evaporates. The templating particles can then be removed and the precursor transformed to the desired material (e.g, silica). The right-hand illustration of FIG. 5 shows a three-phase assembly that further includes gold nanoparticles. Gold nanoparticles can be added to the colloidal suspension and silica precursor that is utilized to form photonic crystals. Then, during the formation of the photonic crystals, the nanoparticles can be incorporated within the non-porous regions of the photonic crystal as shown in FIG. 5.

Incorporation of materials such as gold nanoparticles can allow for the tunability of color depending on the gold nanoparticle concentration. In addition, an optical structure that has an angle dependent structural color from the inverse opal structure as well as an angle-independent plasmonic color from the gold nanoparticles can be obtained.

Figure 6:
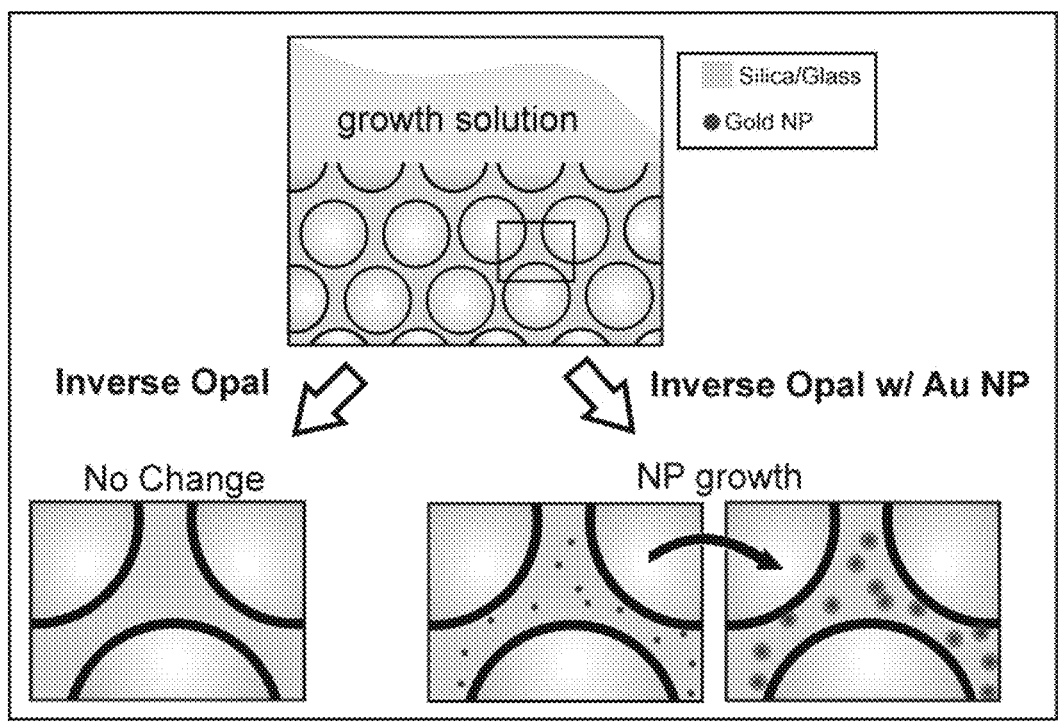
FIG. 6 shows a schematic diagram to grow gold nanoparticles incorporated into the photonic crystal in accordance with certain embodiments.

In certain embodiments, after a photonic crystal containing gold nanoparticles is formed as described above, additional growth of the nanoparticles can be carried out to further enhance the optical response of the photonic crystal. For example, as shown in FIG. 6, a nanoparticle growth solution (e.g., gold nanoparticle growth solution) that wets the photonic crystal can be introduced. In certain embodiments, the hydrophilicity of the photonic crystal can be enhanced by treatment of oxygen plasma prior to introduction of the gold nanoparticles. The photonic crystal can be immersed in a growth solution, such as a dilute, aqueous hydroxylamine ($NH_2OH$) and $HAuCl_4 \times 3H_2O$ solution until the photonic crystal begins to visibly change color due to the growth of the nanoparticles. Without wishing to be bound by theory, although hydroxylamine can reduce $Au^{3+}$ ions (from $HAuCl_4$) into bulk gold (Au), this reduction may be dramatically accelerated by gold surfaces. Thus, new particle nucleation may be suppressed in the growth solution, and most of the added $Au^{3+}$ ions can contribute to the growth of existing nanoparticles (embedded in the silica). Again, without wishing to be bound by theory, the fact that the growth solution increases the size of the nanoparticles in the photonic crystal may indicate that the nanoparticles are accessible to solution even when embedded in the walls of the photonic crystal, possibly implying multiple hierarchies of porosity of the photonic crystal structure. The growth solution leads to an increased nanoparticle size. Accordingly, the regions that have growth of nanoparticles exhibit a rise in the absorption peak attributed to the gold particles.

Figure 7:
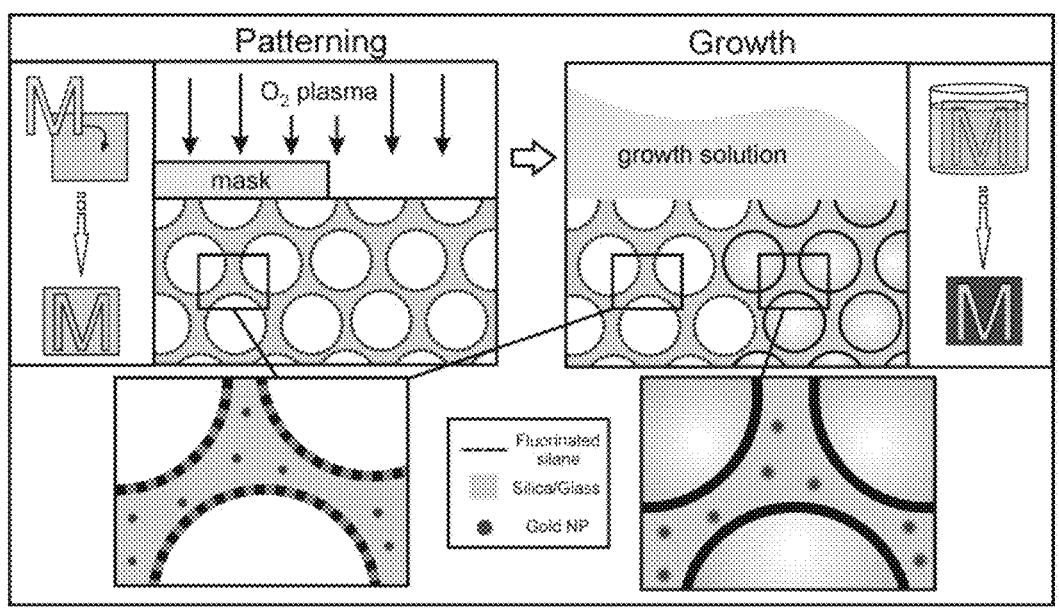
FIG. 7 shows a schematic diagram illustrating patterned growth of gold nanoparticles incorporated into the photonic crystal in accordance with certain embodiments.

In yet another embodiment, selective growth of the nanoparticles can be carried out to further enhance the optical response in only certain regions. For example, as shown in FIG. 7, the photonic crystal grown with nanoparticles can be functionalized in selected regions using, for example, oxygen plasma, as described above. In certain embodiments, the photonic crystal can be functionalized with a desired functional group before a second functional step, such as oxygen plasma. Then, a nanoparticle growth solution (e.g., gold nanoparticle growth solution) can be introduced which wets only the functionalized portions of the photonic crystal. The growth solution can lead to an increased nanoparticle size in only the regions of the photonic crystals that are in contact with the growth solution. In contrast, the regions that are not in contact with the growth solution maintain the original nanoparticle size. Such selective growth of the nanoparticles in one region over that of another region can provide further optical response contrast between the two regions.

Embodiment 3

Mixture of Surface Functional Groups

Figure 8:
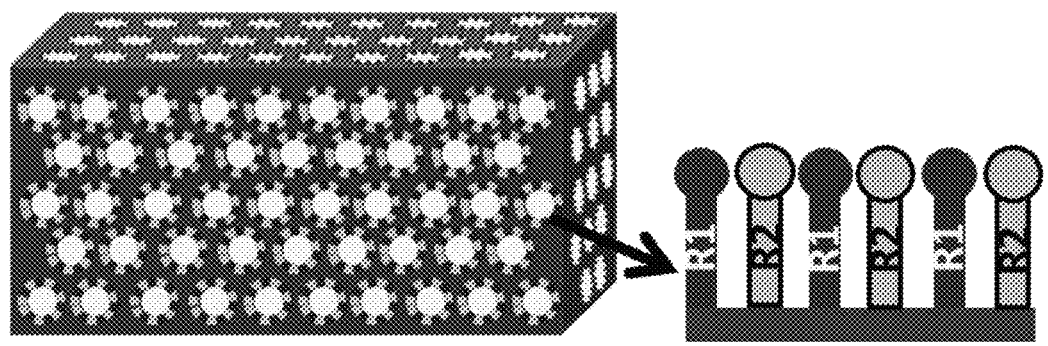
FIG. 8 shows a photonic crystal functionalized with a mixture of different functional groups in accordance with certain embodiments.

In certain embodiments, as shown in FIG. 8, a region of the photonic crystal can be functionalized with two or more different functional groups. For example, molecules having certain functional groups (e.g., $R_1$ and $R_2$) can be prepared. It is possible to vary the relative amounts of the two functional groups (e.g., $R_1$ and $R_2$) on the surface of the photonic crystal pores. The relative amounts of the functional group may be able to provide selective wetting of certain liquids that may not be possible with just a single functional group. In certain embodiments, by using a mixture of two different functional groups, such as $R_1$ and $R_2$ groups, the photonic crystal is able to differentiate between wetting solvents containing different amounts of similar fluids (e.g., two different polar liquids such as water and alcohol mixtures of varying amounts).

For example, the photonic crystals can be functionalized with varying amount of $R_1$ and $R_2$ by preparing a mixture containing the desired relative amounts of $R_1$ and $R_2$, exposing the photonic crystals to the mixture or to the vapors of the mixture. In certain embodiments, the photonic crystal can be exposed two vapors of a first liquid containing a predetermined amount of $R_1$ groups and a second liquid containing a predetermined amount of $R_2$ groups. Adjusting the relative concentration of molecules containing $R_1$ and $R_2$ groups in the respective liquids can alter the relative density of groups on the surface of the photonic crystal.

In certain embodiments, photonic crystals functionalized with more than one functional groups in an appropriate ratio of the functional groups can be utilized to determine the amount of liquid 1 relative to liquid 2 in a mixture of liquids 1 and 2. For example, if $R_1$ groups have greater affinity for liquid 1 and $R_2$ groups have greater affinity for liquid 2, photonic crystals functionalized with greater amount of $R_1$ may allow a mixture containing 95% liquid 1 and 5% liquid 2 to infiltrate whereas a mixture containing 90% liquid 1 and 10% liquid 1 may not be able to infiltrate the photonic crystal.

In certain embodiments, a photonic crystal that has a varying amount of two or more functional groups across the lateral dimensions of the photonic crystal (e.g., certain patterned regions, etc.) may provide a combinatorial approach to identifying unknown solvents. For example, a photonic crystal may have along the x-direction regions that have been functionalized with increasing amounts of $R_2$ groups and along the y-direction, regions that have been functionalized with increasing amounts of $R_3$ groups to form an array of photonic crystal regions that have been functionalized with known and differing amounts of $R_1$, $R_2$, and $R_3$ functional groups. Each of these areas may attract certain mixture of liquids.

Embodiment 3

Designing Wetting Selectivity Through Pore Size Control

In certain embodiments, in addition to controlling the surface chemistries of the pores of the photonic crystal to control the infiltration of liquids (and thus the colorimetric response to liquids), the size of the pores can be utilized as yet another parameter to further fine-tune the wetting selectivity of liquids into the photonic crystal.

When a liquid front propagates through the pores, there is a free-energy tradeoff between the favorable wetting of the solid surface and the unfavorable creation of liquid-air interface. Hence, for a liquid to propagate through the structure, it must overcome an activation barrier. Particularly, many photonic crystals contain a re-entrant geometry where a liquid traversing through the pores of the photonic crystal expands the most. In these regions, the activation barrier can be the highest, which can be calculated for many different photonic crystal structures.

Figure 9:
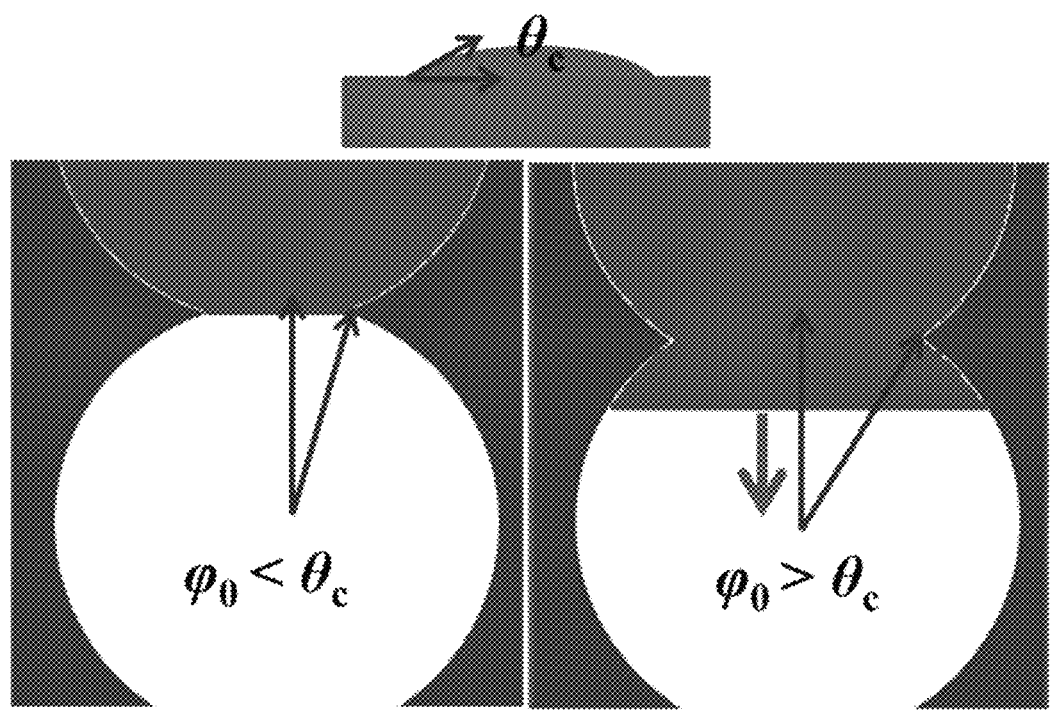
FIG. 9 shows a schematic diagram illustrating the energy barrier encountered for an infiltrating liquid at a reentrant geometry in accordance with certain embodiments.

Taking an inverse opal structure as an example (see FIG. 9), and assuming an energetically favorable liquid-solid interaction (i.e., critical angle, $\theta_c < 90°$), the activation barrier associated with the propagation of the liquid front through the pore exists if $\theta_c$ is larger than the azimuthal angle ($\phi_0$) subtended by the smaller regions of the pores (i.e., re-entrant geometry), shown schematically in FIG. 9 as the neck between the pores. For a given liquid and pore surface functionality, the corresponding $\theta_c$ defines a critical neck angle, smaller-than-which the liquid front will not be able to pass from one pore to the next.

As shown, $\theta_c$ can be estimated by measuring the contact angle of the infiltrating liquid with a flat substrate. $\phi_0$ can be calculated for a number of different structures, including and not limited to inverse opal structures, body-centered cubic, simple cubic structures that can be formed by forming similar "neck" regions as shown in FIG. 9.

In certain embodiments, a photonic crystal with uniform surface chemistry has the capacity to colorimetrically differentiate liquids based on differences in $\theta_c$ of less than 10°, or less than 5°, or less than 2°, or less than 1°. Taking ethanol-water mixture as an example, an inverse opal photonic crystal with uniform surface chemistry with the ability to differentiate liquids based on differences in $\theta_c$ less than 5° corresponds to the ability to differential just 5% changes in the relative amounts of ethanol and water (i.e., between 90% and 95% ethanol in water).

Accordingly, a photonic crystal having a long range order with well-defined pore sizes and well-defined re-entrant geometry have a significant advantage over that of a structure that utilizes a random network of pores having different sizes. In a random network of pores, there is a high likelihood that an infiltrating liquid will find a nearby pore that has sufficiently large enough pore size to continue its path along the network of pores. In contrast, in a perfectly symmetric photonic crystal structure with exactly the identical pores throughout, the transition between a photonic crystal that is completely impervious to liquid infiltration (e.g., displaying iridescent color) and one that is completely infiltrated (e.g., transparent, showing the color of the underlying substrate) at equilibrium can occur over an infinitesimally narrow range of liquid contact angles ($\theta_c$) because the free-energy landscape associated with fluid percolation through the pores will be the same at every identical unit cell.

Figure 10:
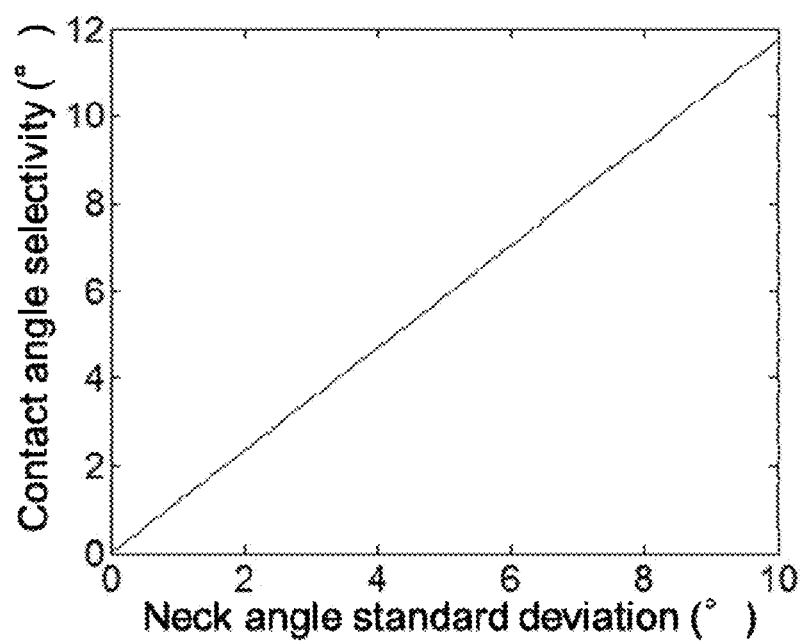
FIG. 10 shows a simulated plot of contact angle selectivity as a function of neck angle standard deviation in accordance with certain embodiments.

Fabricated photonic crystals do display some degree of both short-range (<mm scale) and long-range (>mm scale) variations in the pore sizes. However, these variations can be taken into account to provide further control in the wetting behavior. For example, an inverse opal structure having an average neck angle of 20° can be fabricated with some variation in the neck angles. FIG. 10 shows a plot of predicted liquid selectivity limits (expressed in terms of contact angle) as a function of the neck-angle standard deviation using a mean neck angle of 20°, where in this non-limiting case, the selectivity limits were defined as the difference in contact angles between those that resulted in 99.9% pore filling (defining the colorimetrically "filled" state), and those that produce fluid-connectivities lower than the percolation threshold for an fcc lattice (12%) (defining the colorimetrically "empty" state). As shown, there is a linear relationship between the selectivity with standard deviation of neck angles. In other words, as the variation in the neck angles increases, the capacity to differentiate liquids based on differences in $\theta_c$ also decreases, generally with a linear relationship. In practice, a photonic crystal can be fabricated with certain tolerance level of the pore size variation, and this variation can be taken into account either theoretically or experimentally in determining the photonic crystal's ability to differentiate between different liquids.

Embodiment 4

Vertical Patterning of Different Functional Groups

Figure 11A:
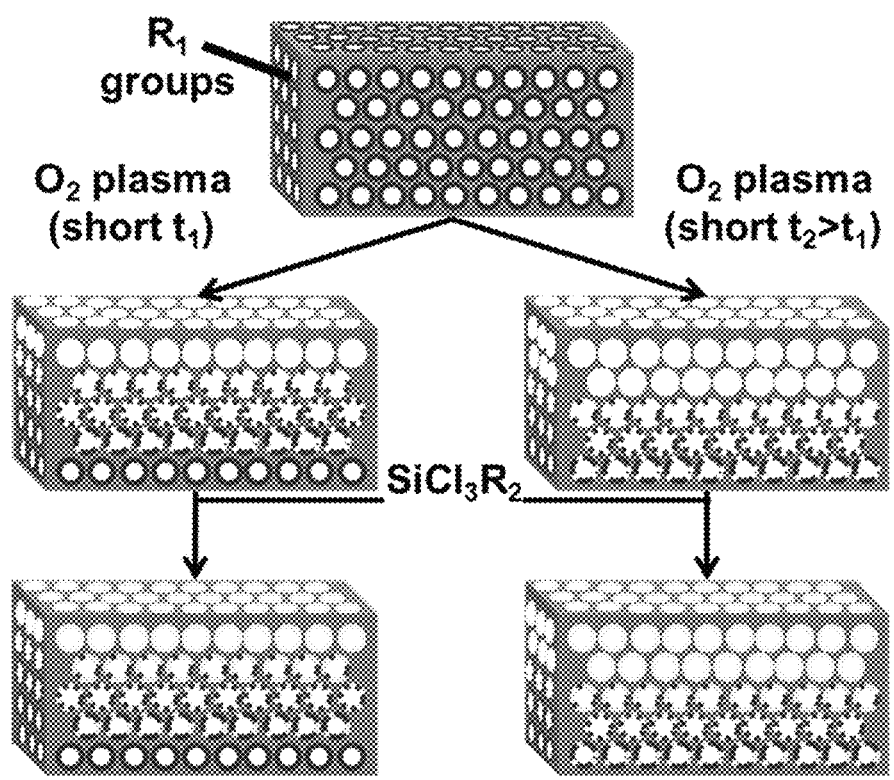
FIG. 11A shows a schematic diagram illustrating a method to pattern a photonic crystal having a vertical gradient of functional groups in accordance with certain embodiments.

In certain embodiments, vertical gradients of wettability can be generated, which in turn can provide added benefits of enhanced optical response. Vertical gradient of wettability can be formed by changing the number and/or type of functional groups along the vertical (i.e., thickness) direction of the photonic crystal film. As shown in FIG. 11A, a photonic crystal is patterned with a first functional group $R_1$.

Then, the photonic crystal is treated to remove the $R_1$ groups from only a top portion of the photonic crystal, such as by using short plasma-exposure times, but under conditions that are insufficient to completely remove the existing groups throughout the depth of the structure. The depth to which the first functional groups are removed can be controlled as desired. Taking short plasma-exposures as an example, longer exposure times can remove the first functional groups that are deeper within the photonic crystal whereas shorter exposure times can remove first functional groups that are only near the top surface of the photonic crystal. Removal of the first functional groups as described above may provide a gradient of the first functional group that gradually increases as a function of thickness. Then, the photonic crystal can be functionalized with a second functional group. Near the upper portion of the photonic crystal, the pores may be predominantly functionalized with the second functional groups whereas the bottom of the photonic crystal may be predominantly functionalized with the first functional groups.

Figure 11B:
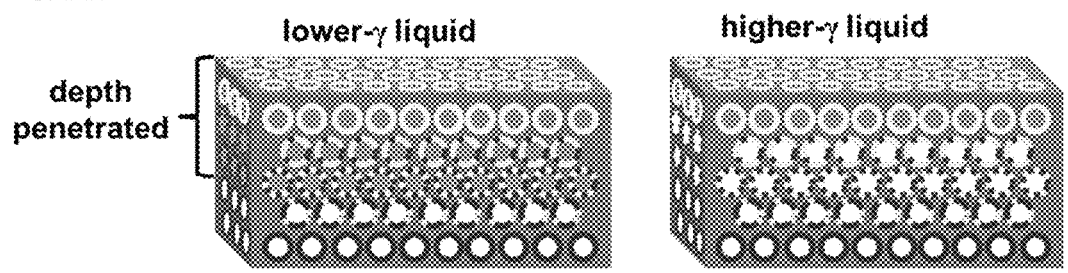
FIG. 11B shows a schematic diagram of the selective depth penetration of an infiltrating liquid for a photonic crystal having a vertical gradient of functional groups in accordance with certain embodiments.

In certain embodiments, the vertical gradient described above can be provided to a photonic crystal that increases its thickness along the lateral dimension. For instance, assuming a photonic crystal that changes its thickness from only four layers to six layers along a lateral dimension (e.g., left to right). If the vertical gradient is provided so that the photonic crystal uniformly functionalized with $R_1$ groups is treated to remove the $R_1$ groups from only the top four layers of the photonic crystal followed by functionalization with $R_2$ groups in only those removed regions, then the left portion of the photonic crystal will have its entire thickness functionalized with $R_2$ whereas the right portion of the photonic crystal will have its first four layers functionalized with $R_2$ groups with the bottom two layers functionalized with $R_1$ groups. In practice, the right portion of the photonic crystal may gradually change from the top to bottom from a predominantly $R_1$ functional group to a predominantly $R_1$ functional group. Then, as shown in FIG. 11B, photonic crystals having vertical gradients of chemistry (e.g., in which the wettability decreases with depth) can display distinct partial infiltration patterns in incrementally different liquids, each penetrating a fixed depth. In other words, as shown in FIG. 11B, the photonic crystal near the left edge having four layers can be completely filled with an infiltrating liquid whereas the photonic crystal near the right edge can be filled with an infiltrating liquid near only the top four layers of the photonic crystal, leaving the bottom two layers of the pores unfilled with the liquid.

As discussed above, if the infiltrating liquid provides a refractive index match with the photonic crystal, filling of the photonic crystal can lead to a transparent material. In that case, the region of the photonic crystal near the left edge in FIG. 11B may appear transparent while the photonic crystal near the right edge of FIG. 11B can continue to an exhibit a color, providing a color contrast across the lateral dimension for the same infiltrating liquid.

Even if the infiltrating liquid does not provides a refractive index match with the photonic crystal, the different regions will exhibit different colors due to the differences arising from the filled and unfilled layers.

Accordingly, as schematically shown in FIG. 11B, by producing a photonic crystal that increases its thickness across the lateral dimension and providing a vertical gradient in the photonic crystal, many distinct patterns can be observed depending on depth of penetration of the infiltrating liquid. Different thickness can be produced by evaporating the solvent from the colloidal suspension where the substrate is placed at an angle, or laying down multiple sheets of photonic crystal, or by forming the photonic crystal in sequential steps with a step-like profile.

Figure 11C:
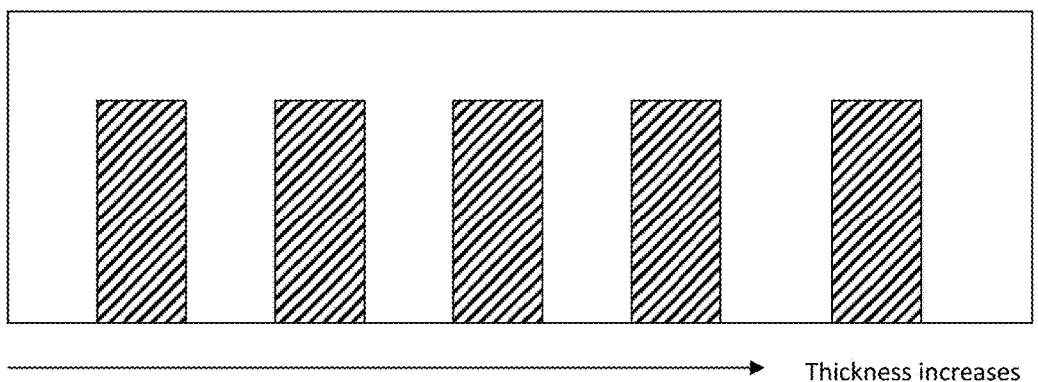
FIG. 11C shows a schematic illustration of "teeths" pattern, each having a vertical gradient of functional groups that increases in thickness from left to right in accordance with certain embodiments.

In certain embodiments, as shown in FIG. 11C, after a vertical gradient is formed, the photonic crystal can further be patterned in the lateral dimension. For example, the photonic crystal having a vertical gradient can be provided with a mask as shown in FIG. 3B and the unmasked portions exposed to an etchant (e.g., oxygen plasma) to remove the vertical gradient in the unmasked portion. Hence, only specific desired portions of the photonic crystal is patterned with a vertical gradient of surface functionalities (indicated as the regions with stripes in FIG. 11C). In some embodiments, the remaining areas of the photonic crystal (indicated as the white portion) can be further functionalized with groups that does not allow infiltration of any of the liquids of interest.

This particular embodiment possesses two important advantages with respect to the colorimetric differentiation of liquids: i) the minimum colorimetrically discernable difference in wettability can be smaller for vertical gradients than for uniformly functionalized photonic crystals (for the same short-range variability in the neck-angle, $\phi_0$); and ii) a single vertical gradient can produce many distinct patterns in many different liquids. Vertical gradients allow enhancement of the colorimetric selectivity, not by decreasing the range of $\theta_c$ over-which partial infiltration patterns are observed, but by transforming partial infiltration patterns to a form that become easy to mutually distinguish visibly (i.e. have countable differences).

Embodiment 5

Paints for Combined Horizontal and Vertical Patterning

In certain embodiments, a large numbers of photonic crystal particles can be fabricated, followed by any of the functionalization discussed above. While the previous disclosure focused on forming large sheets of photonic crystals, it is within the scope of the present invention to form much smaller particles of photonic crystals, functionalizing the photonic particles, dispersing the functionalized photonic particles in a suitable fluid, and utilizing the mixture as a photonic crystal applicator liquid, such as a photonic crystal paint to be applied on any desired surfaces. Accordingly, whereas the discussion above focused on forming photonic crystals on a specific substrate shape, the photonic crystals can be applied in any arbitrary shape that is desired without being limited to the particular shape and geometry of the underlying substrate.

In certain embodiments, two or more paints containing photonic crystal particles that have been functionalized with different functional groups can be utilized. For example, a first paint can include photonic crystal particles that have hydrophobic functional groups whereas a second paint can include photonic crystal particles that have hydrophilic functional groups. The two different paints can be applied in any manner, such as on different lateral locations or on top of each other to mimic vertical gradient functionalization. Any number of different paints, each having different photonic crystal particles having predetermined functionalities that are different from each other can be envisioned.

Taking the example of applying a sign with road sign first with a first photonic crystal paint having hydrophilic functional groups followed by a second photonic crystal paint having hydrophobic functional groups painted with the words "CAUTION: WET," the hydrophilic particles would become saturated with water when raining, and lose their color, while the hydrophobic particles would remain the original color. As a result, the sign would change to exhibit the words "CAUTION: WET" when it rains or the environment is heavily saturated with water.

In some embodiments, photonic crystal particles can be fabricated and dispersed in a paint. Thereafter, the photonic crystal particles can be applied to a surface and any of the surface functionalization techniques discussed above (e.g., lateral patterning, vertical gradient functionalization, etc.) can be carried out.

Numerous different methods for forming photonic crystal particles can be envisioned. For example, colloidal co-assembly can be applied to structured surfaces, such as parallel grooves and holes, to produce hierarchically-structured inverse opals. FIGS. 12A to 12C show examples of microstructures etched in Si by deep reactive ion etching (DRIE), as interconnecting walls which define 'brick' and 'honeycomb' cavities. FIG. 12D illustrates schematically the co-assembly of colloidal particles and dissolved matrix into a microstructured surface. FIG. 12E illustrates schematically the inverse opal 'bricks' after thermal calcination to remove the polymer template. Finally, FIG. 12F shows an example (SEM) of a $SiO_2$ inverse opal structure (300 nm pores) deposited into grooves of 4 μm width, after thermal calcination. FIGS. 13A to 13C show discrete 'bricks' assembled in a polymer template structure (consisting of SU-8 epoxy photoresist walls). FIGS. 13D to 13F show discrete 'hexagons' also assembled in a SU-8 polymer template. The formed photonic crystals particles can be ejected from the templates to form an applicator liquid (e.g., paint) as discussed above.

Figures 14A, 14B:
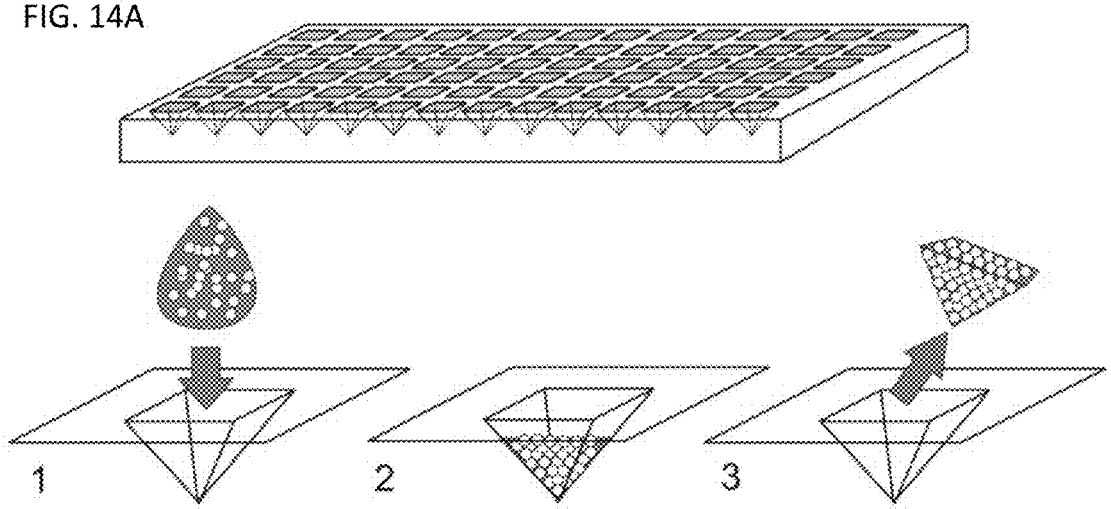
FIG. 14A-B shows a schematic diagram illustrating a method for obtaining photonic crystal particles in accordance with certain embodiments.

In addition to a microstructure of regular bricks and hexagons, a microstructure which may be more practical and useful is an array of inverted pyramid cavities. Such surface structures are relatively easy to produce over large areas, and may allow for easier release of the particles from the mold. In certain embodiments, a large sheet of microstructured cavities for the colloidal co-assembly suspension to be cast into, such as shown in FIG. 14A for an array pyramidal cavities. After deposition of a colloidal suspension (plus dissolved matrix) into each cavity (FIG. 14B, step 1), and evaporative casting of the individual inverse opal particles (FIG. 14B, step 2), the particles could be removed from the molding sheet (FIG. 14B, step 3), calcined (300-500° C.) and dispersed into a paint suspension. Upon spreading on a wall or other flat surface, the individual inverse opal particles would produce an iridescent color in the dried paint, which may be directional-dependent (ie; changes color depending on the viewing angle) depending on the general orientation of the particles in the paint.

The present disclosure provides methods for patterning many different surface functional groups in 3D porous structures. The technique can be used to create technology serving a vast array of purposes. Through a simple, repeatable process, fluids can be confined and manipulated in a structurally homogeneous material. Once selective infiltration of fluids is achieved, these fluids themselves can also be used as a carrying medium or mask for further functionalization reagents.

The methods described herein will readily be apparent to one of ordinary skill in the art to be applicable to a wide variety of porous media, such as mesoporous ceramics and silica gels used in thin-layer chromatography, making it suitable to a host of different applications.

Applications

Numerous different applications are envisioned to arise from the present disclosure.

Encryption of Optical Messages:

One of the applications of this technology that may be possible is in a multilevel document and art authentication and message encryption. Secret messages can be encoded in the structure through its local surface functionality. As the surface functional groups considered here have no direct effect on the optical properties of the photonic structure, no message would be viewable until the photonic structure is immersed in a solvent. Depending on the number of different functional groups used, different solvents could reveal different messages, with only the intended recipient knowing the correct solvent in-which to read the message. Upon solvent evaporation, the encoded message disappears again returning to the original appearance of the colored region.

Accordingly, no message may be visible in air, while n messages may be visible from immersion in n-different solvents with a sample having n+1 different pore-functionalities. More messages can be encrypted with relatively few functional groups using controlled mixing of functionalities, either by grafting or spatial mixing, or using wicking from designated starting points through selectively connected domains to define multiple distinguishable messages in the same sample.

Colorimetric Indicator for Liquids Based on Wetting Properties:

A photonic structure strip, able to colorimetrically distinguish between liquids with different wetting properties (e.g, various alcohols, acetone, water and their mixtures), can be very effective as a field-test for the identification or authentication of liquids. This could be useful, for example the identification of small spills or unlabelled/abandoned containers that are frequently found in communal laboratory environments. The strip would give an instant optical indication of the type of organic liquid present (for example, differentiating ethanol or isopropanol from their lethal counterpart, methanol), as pH paper does for pH. As wettability is a generic property of liquids, this type of field test could be tailored to give colorimetric determination of the composition of liquids across a wide variety of classes (e.g. identifications of unlabeled/spilled laboratory solvents, in-situ identification of liquid explosives, diagnostics for bodily fluids such as blood or urine based on their wetting properties, etc.). This technology could also be useful for the authentication of liquid formulations again forgery, which could be applied in a variety of industries (e.g. liquid formulation pharmaceutical products, field test for the validation of the grade and quality of engine fuels, liquors, etc.).

Invisible Reconfigurable Microfluidic Channels:

As this material is able to confine liquids in areas of compatible surface functionality, multiple channels can be written on one chip purely through the definition of the surface chemistry. Propagation through the channels can occur without external pumping through capillary processes (i.e. wicking). As the channels are defined through surface functional groups only, they can easily be erased and rewritten in a different configuration.

Microfluidic/Chromatographic Channels with Fixed Configurations and Patterned, Reconfigurable Functionality:

Material precursors can be selectively infiltrated only into regions of compatible functionality. After curing or solidification, permanent channels (where the material precursor did not infiltrate) are defined in the microporous structure. These channels can be used for applications where a microporous medium integrated into microfluidic channels is desired (e.g. intra-microfluidic chromatography columns for chemical separation). This also can be a useful technique for defining channels containing a porous medium with well-defined periodicity.

Extension to Other Porous Inorganic Media:

This patterning technique can be applied to any interconnected porous medium (where all or some pores are plasma/fluid-accessible) that has compatibility with oxygen plasma or similar etching technique and the ability to absorptively interact or to react with functional monolayers. This could be extended beyond silica inverse opals to mesoporous materials (silica, titania etc.), inorganic xerogels and aerogels such as those used in thin layer chromatography etc., and may find further uses in those materials.

Extension to Other 3D Patterning Techniques:

The present patterning technique in a three-dimensionally porous structure could be varied for example by applying the self-assembled monolayers through liquid reactions. Monolayers may be able to be selectively added rather than removed, particularly in materials with smaller pores, owing to low diffusion through the porous network.

Time Dependent Color Change to Determine Volatility:

The evaporation of infiltrated liquid can produce a change in color, which can provide a simple method for determining the evaporation rate of a fluid.

Selective Wetting to Detect Particle (e.g., Protein) Adsorption:

If particles such as proteins, viruses, colloidal particles and the like adsorb onto the photonic crystal surface, this can effectively change the pore size, which can in turn change the type of fluids that can infiltrate the photonic crystal as well as the colorimetric response. Hence, the photonic crystals can be useful as a diagnostic tool to determine the presence of any known particles in an infiltrating liquid. Specificity can be added by functionalizing the surfaces with known functional groups that bind to a specific class of materials (e.g. anti-bodies, particle tags, etc.).

Enantioselective Colorimetric Indicator:

Chiral liquids can change its contact angles depending on the amount of S and R molecules that are present. Accordingly, the photonic crystal of the present disclosure can serve as a fast diagnostic to determine the relative amount of S and R molecules inside a fluid.

The applications listed here represent the tip of the iceberg of the new technologies that may be possible in areas such as authentication and security, encryption, fluid-manipulation and simple diagnostics.

EXAMPLES

Example 1

To study the wetting interfaces present in the patterned photonic structures, channels of SiOH functional groups were patterned into a photonic crystal (PC) that was functionalized uniformly with (1H,1H,2H,2H-perfluorooctyl)silyl (13FS) groups. The pores of the 13FS-functionalized PC were found to be sufficiently nonwetting to resist infiltration of most solvents, including pre-cured PDMS (Sylgard 184). By selective infiltration of PDMS into the ROH-functionalized channels followed by thermal curing, detailed measurements of the resolution of the wetting-non-wetting interface was possible.

Figure 15A:
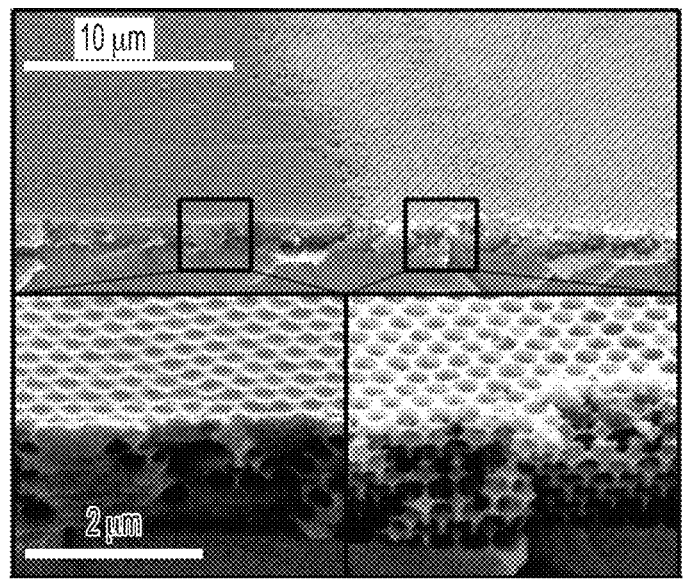
FIG. 15A-E shows SEM, optical images and spectra of a selectively functionalized and selectively infiltrated three-dimensional photonic crystal in accordance with certain embodiments.
Figure 15B:
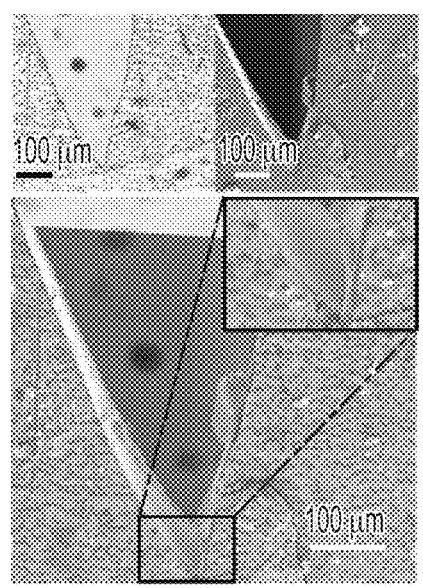
Figure 15C:
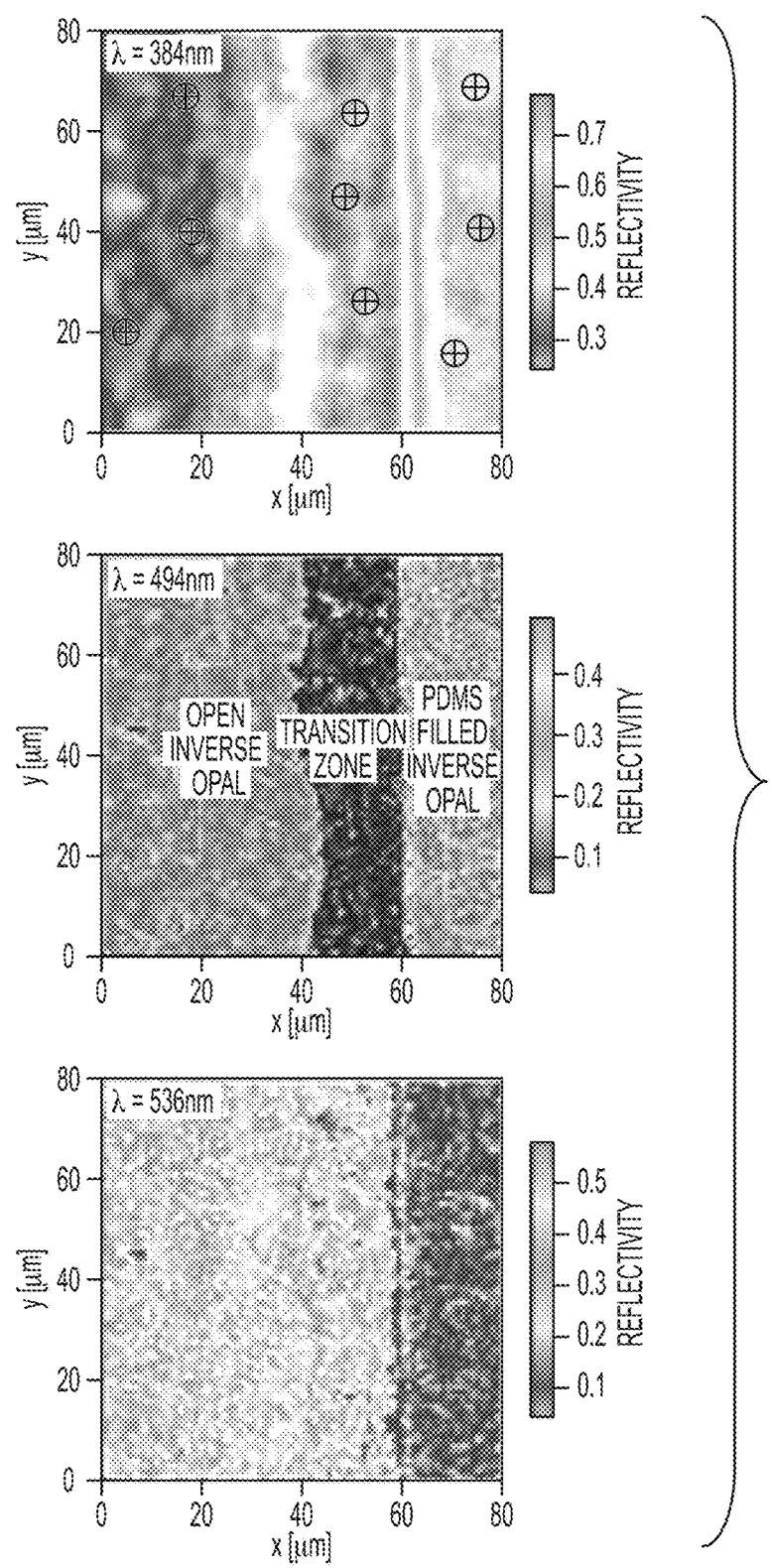
Figure 15D:
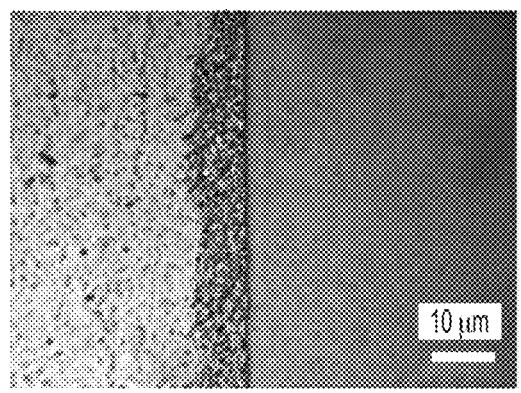
Figure 15E:
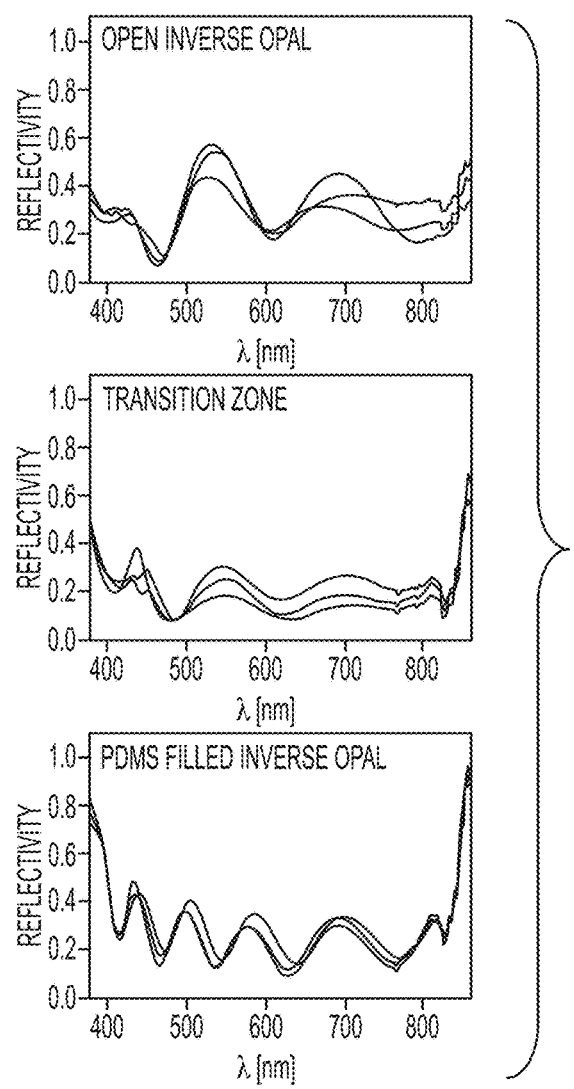

FIG. 15A shows SEM images of the infiltrated channels and interfaces. PCs of low to moderate thickness (<15 layers) is shown. Particularly, FIG. 15A shows SEM images showing selective infiltration of PDMS into a 13FS/ROHbifunctional photonic crystal, cured after immersion. FIG. 15B shows comparison of the PDMS mask (SEM) to the optical pattern observed (optical image), visualized by infiltration) after plasma-etching through the mask. FIG. 15C shows spectral scans of the interfacial region as well as the completely infiltrated and completely non-infiltrated regions. FIG. 15D shows the corresponding optical image, and FIG. 15E shows representative spectra from each region.

As shown, interfaces are well defined over a large scale and the transition between complete infiltration and non-infiltration can be as small as 10-20 periods (5-10 μm). In particular, the resolution was estimated by comparing the dimensions of the PDMS mask to the final infiltration interface using optical and scanning electron microscopy. FIG. 15B also shows that even very small features are transferred accurately within a resolution of at least 10 μm.

Example 2

To demonstrate the encoding capabilities of the photonic structure with multiple functional groups, $SiO_2$ inverse opals were patterned with combinations of ROH surfaces and those treated with four different alkylchlorosilanes with decreasing hydrophilicity: trimethylchlorosilane (TMS), (3,3,3-trifluoropropyl)trichlorosilane (3FS), (n-decyl)trichlorosilane (DEC), and 13FS.

FIG. 3 again illustrates the patterning procedure for a 13FS/TMS/ROH-trifunctional photonic crystal.

When a solvent penetrates the pores of a PC, the refractive index-contrast is reduced and the optical path-length between periods increases, resulting in a redshifted and diminished reflection peak for a PC of finite thickness. Spectra of regions with the three different functional groups are shown in FIG. 6 in air and upon immersion in water and ethanol.

Figure 16A:
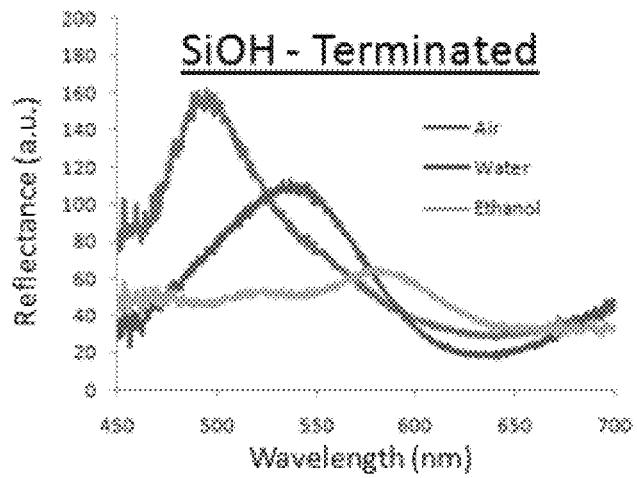
FIG. 16A-C shows reflectance spectra of a selectively functionalized three-dimensional photonic crystal, selectively infiltrated by different fluids in accordance with certain embodiments.
Figure 16B:
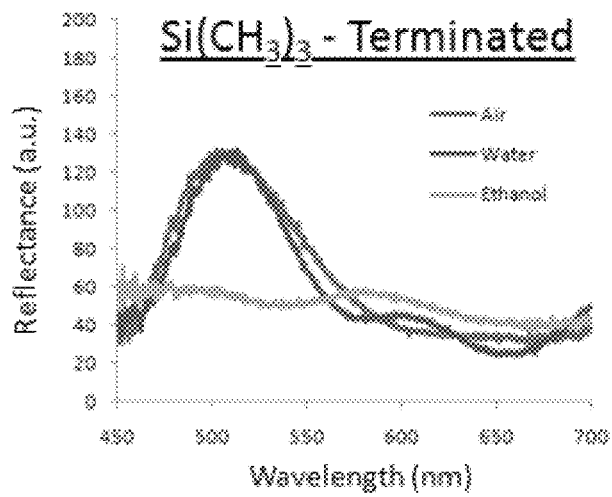
Figure 16C:
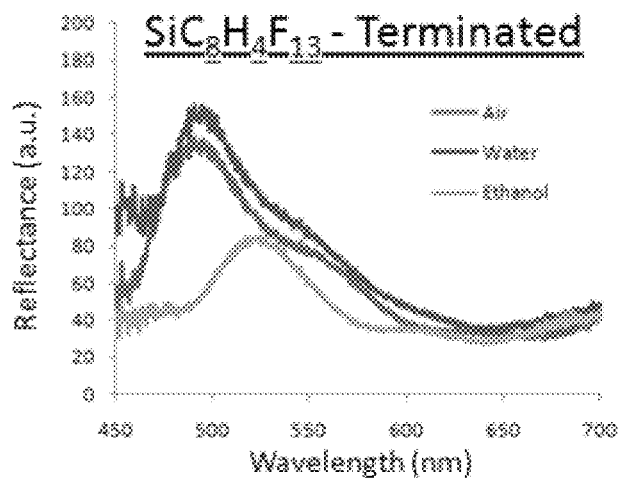

The 13FS-functionalized opal shows little shift in all three solvents (FIG. 16C), while the ROH-functionalized area shows increasing shift in water (n=1.33) and ethanol (n=1.36) (FIG. 16A). The TMS-functionalized area shows no spectral shift in water while displaying a large shift in ethanol (FIG. 16B), similar to the ROH-functionalized area.

This indicates that while water does not enter either TMS of 13FS-functionalized areas, ethanol enters the TMS areas while not entering the 13FS area.

The same result as with ethanol was observed in hexane (and liquids with lower polarity) and un-cured PDMS resin.

With PDMS, selective liquid infiltration was also verified with SEM after curing.

Example 3

To demonstrate the concept of document authentication and multilevel message encryption, the word "INK" was patterned with 13FS functional groups. Moreover, a letter "W-" having TMS functional groups was encrypted in front of the word "INK".

Figure 17A:
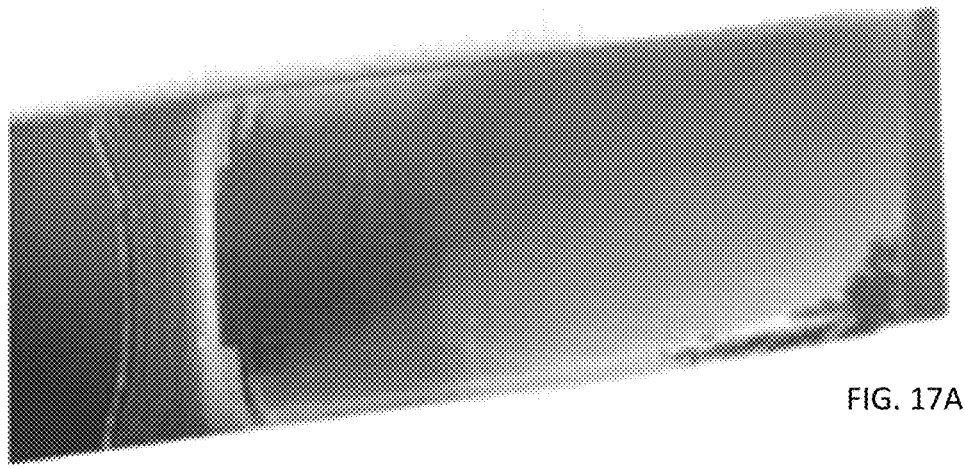
FIG. 17A-C shows an example of a two-level encryption presenting two different encrypted messages using immersion of selectively functionalized three-dimensional photonic crystal in different solvents in accordance with certain embodiments.

The resulting structure shows no distinguishable pattern in air (see FIG. 17A).

Figure 17B:
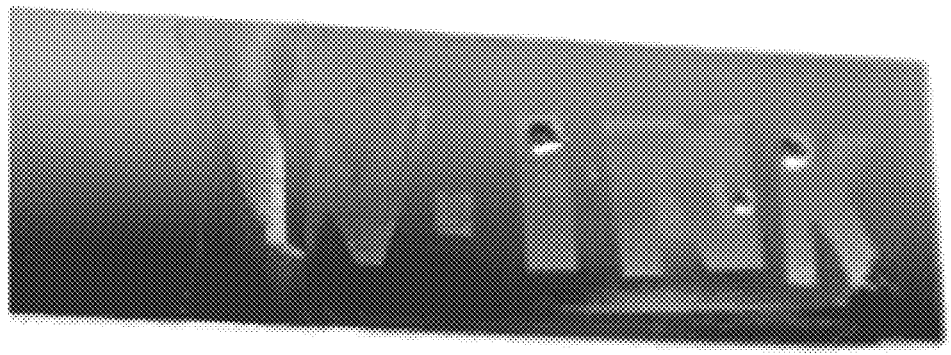
Figure 17C:
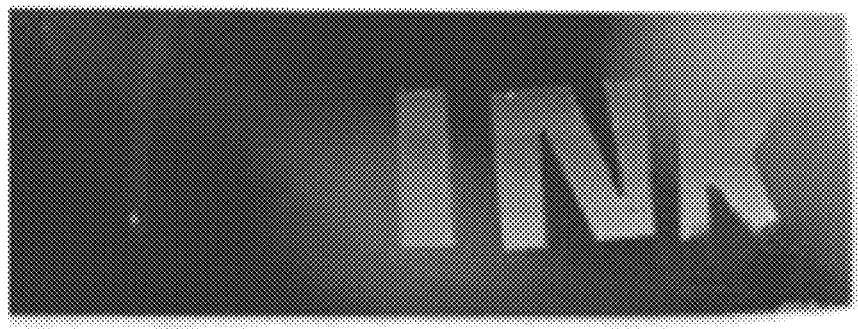

When exposed to ethanol, the structure shows "INK" due to the contrast between 13FS-TMS/ROH regions as shown in FIG. 17C.

When exposed to water, "W-INK" appears due to the contrast between 13FS/TMS-ROH regions, as shown in FIG. 17B.

The more functional groups in the message, the more highly specific the solvent choice must be and also, the more different solvent-specific messages can be simultaneously coded into the same material.

Example 4

FIG. 18 shows an expanded example of this message encryption: a sample having four levels of encryption due to selective surface modifications with five functional groups, thus displaying four messages. The functional groups included TMS (patterned as "W-"), 13FS (patterned as "I"), DEC (patterned as "N"), 3FS (patterned as "K"), and ROH (patterned as the background). With increasing number of functional groups, it is more desirable to create a continuum of wettability using miscible liquid mixtures (e.g. water and ethanol) with different volume-ratios rather than using a range of pure solvents that distinguish between all pairs of functional groups with adjacent wettabilities. This avoids the use of potentially hazardous liquids in reading the encrypted messages.

Using this approach, a different text in the sample can be observed each time the wettability of the solvent passed the threshold for infiltration of each functional group.

Figures 18A, 18B, 18C, 18D, 18E:
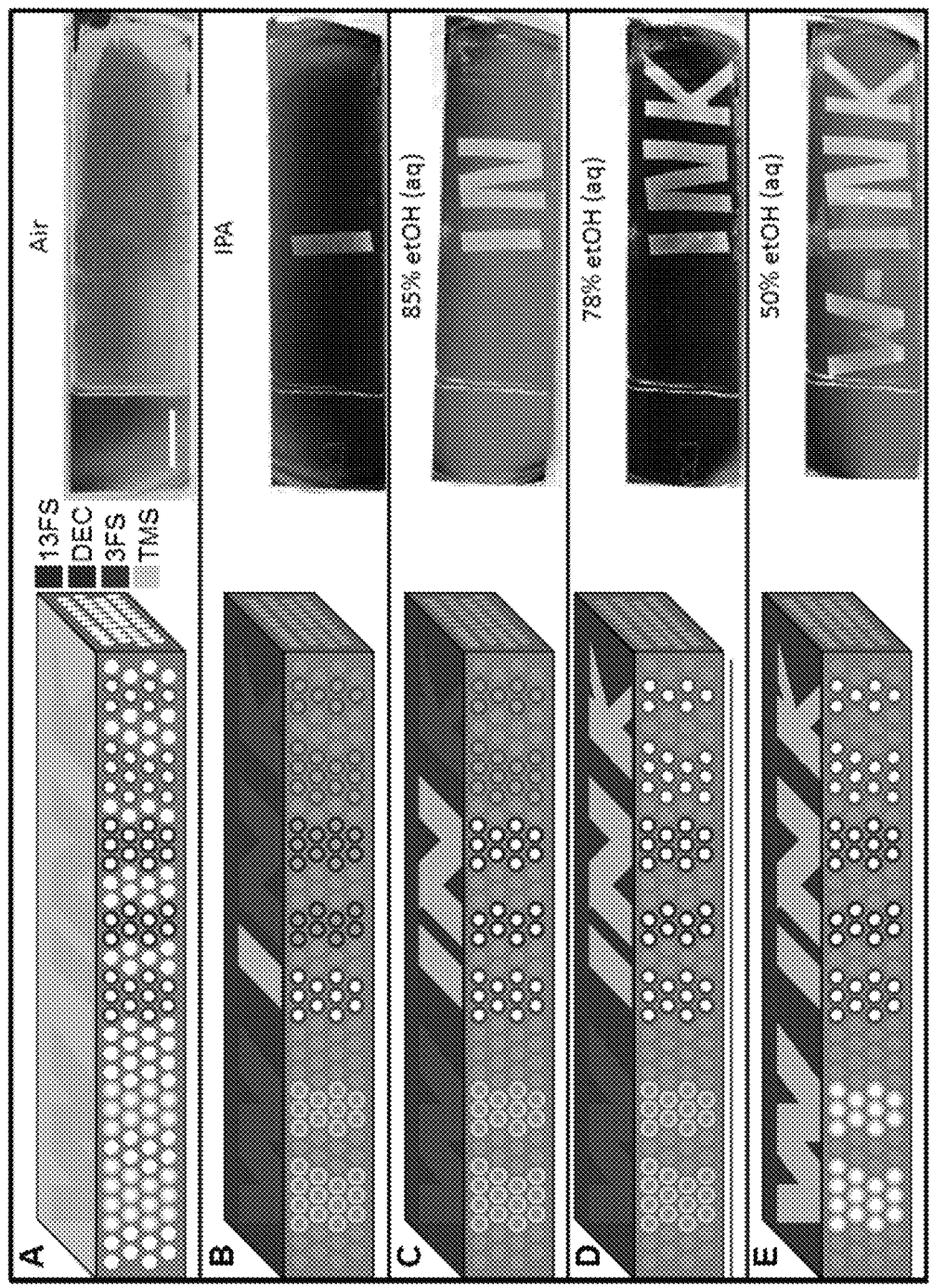
FIG. 18A-E shows an example of a four-level encryption presenting four different messages using immersion of selectively functionalized three-dimensional photonic crystal in accordance with certain embodiments.

As shown in FIG. 18E, in aqueous ethanol mixtures containing less than ~70% ethanol in water, the word "W-INK" is visible from TMS/3FS/DEC/13FS all resisting infiltration, while the ROH background is infiltrated.

As shown in FIG. 18D, in a ~78% (vol) aqueous ethanol solution, the TMS is infiltrated, while 3FS, DEC, and 13FS are not, thus "INK" appears as the word.

As shown in FIG. 18C, in a ~85% (vol) aqueous ethanol solution, both TMS and 3FS are infiltrated and the word reduces to "IN".

As shown in FIG. 18B, in isopropyl alcohol, all but the 13FS is infiltrated, resulting in the word "I".

For applications in authentication, one could mark the document/package/art with a small piece of the photonic crystal and require several specific, different patterns to appear in several different solvents (or mixtures) for validation of the package.

Example 5

By employing the similar principle as that of Example 4, photonic crystals can also be used as a cheap, reusable pH-paper-like indicator for organic solvents. Here, we demonstrate that differences between different surface functionalities can be adjusted to match subtle differences between the wettabilities of otherwise similar liquids. Below we demonstrate a strip that visibly distinguishes between different alcohols, including methanol and ethanol.

Figure 19:
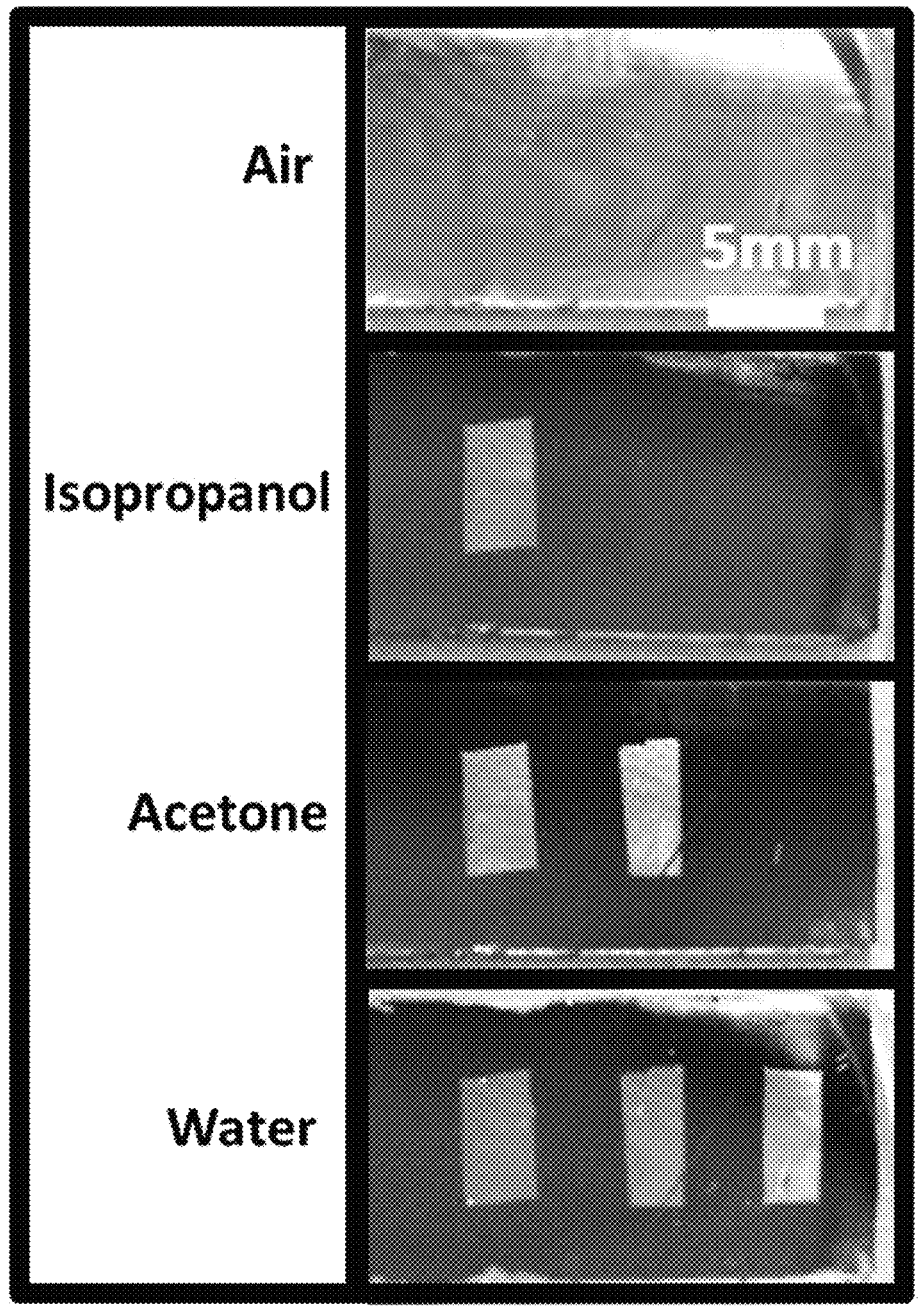
FIG. 19 shows a solvent identification "paper" using a selectively functionalized three-dimensional photonic crystal in accordance with certain embodiments.

FIG. 19 shows a photonic crystal that has been divided into three areas, having been treated with (from left) 13FS, DEC, and 3FS silanes.

While 3FS-areas can distinguish between water (no infiltration) and most organic solvents (infiltration), DEC-areas resist infiltration to water and acetone and total infiltration by isopropyl alcohol. The 13FS-stripe is not infiltrated by any of these solvents.

This type of functionalized PC-strip, along with pH paper for acids and bases, would be very effective in the identification of small spills or unlabelled/abandoned containers that are frequently found in a communal cleanroom environments, where alcohols and acetone are commonly used organic solvents. Laboratories commonly using a larger number of solvents would require a W-Ink indicator having more encoded functional groups. The samples shown in FIGS. 18 and 19 demonstrate the potential for high selectivity of such an indicator, showing large visible difference with similar liquids such as 78% vs 85% ethanol in water (FIG. 18) and water, acetone, and isopropanol (FIG. 19).

Example 6

Owing to its ability to allow the infiltration of solvents in a selective manner, a selectively functionalized photonic structure also has potentially interesting applications in microfluidics.

Fluidic channels containing a highly regular microporous network with modifiable chemical functional group can be defined in two different ways, denoted here as "visible channels" and "invisible channels".

Fluid transport through the channels can occur through capillary forces (wicking) or through active pumping.

Visible channels were formed by patterning a homogeneous inverse opal sample with 13FS functional group in the channel regions and ROH functional group outside. Submerging the sample in un-cured PDMS resulted in infiltration of the ROH regions while the 13FS regions remain un-infiltrated (see FIG. 20A, top). After curing, it was possible to manually peel off the PDMS overlayer, naturally cleaving at the top-surface of the inverse opal, resulting in a smooth film with porous channels exposed (see FIG. 20A, middle). Thereafter, the porous regions were exposed to oxygen plasma and subsequently functionalized with desired functional groups (see FIG. 20A, bottom).

FIGS. 20B and 20V show optical and SEM images, respectively, demonstrating the high contrast achieved by the process up to about 10 μm resolution.

Although only one particular functionality is shown in this specific example, similar to the previous examples, channels with many different functionalities can be provided on the same chip allowing for selective transport of different solvents in specially designated channels.

FIG. 20D shows 60% ethanol in water provided in a saturated ethanol atmosphere wicking up a channel that has been ROH-functionalized.

Example 7

Figure 21:
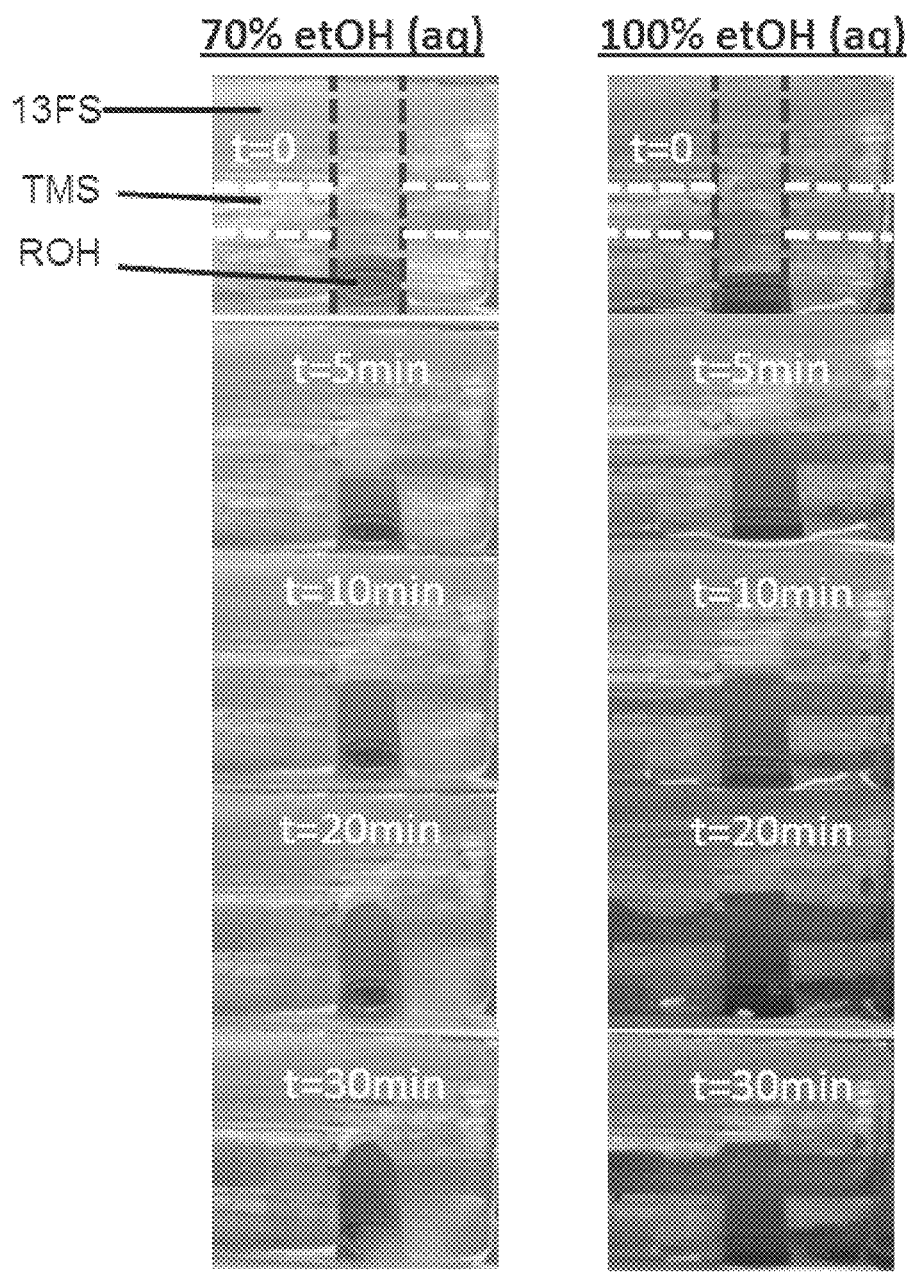
FIG. 21 shows an "invisible" microfluidic channel formed by selectively functionalizing a three-dimensional photonic crystal and wicking fluid through the structure in accordance with certain embodiments.

Since 13FS functionality in the pores of PC allows for its resistance to infiltration of most solvents, it can be used to define the walls of "invisible" channels. FIG. 21 shows a structurally uniform PC containing two invisible channels defined with ROH functionality (vertical) and TMS functionality (horizontal). 70% ethanol in water wicks only through the vertical, ROH channel, while pure ethanol wicks through both channels. Note that neither solvent penetrates the channel walls, having 13FS functionality.

Hence, "invisible channels" are defined using chemical functionality for lateral confinement. 13FS-functional groups, resisting infiltration by most solvents, are used in the channel walls. While they lack the longevity and robustness against chemical contamination of the visible channels (i.e. it is more difficult to remove contaminants without removing the channel functionality), they have the advantage that they can be both chemically and configurationally repatterned, through the same erasing-rewriting procedure described above.

Example 8

Gold nanoparticles were synthesized and added to the colloidal suspension and silica precursors prior to deposition, to create hierarchical inverse opal structures via a three-phase co-assembly method.

NP Synthesis:

All glassware used in these preparations was thoroughly cleaned in aqua regia (3 parts HCl, 1 part $HNO_3$), rinsed in triply distilled $H_2O$, and oven-dried prior to use. The following stock solutions were prepared from triply distilled $H_2O$: 1.0 mM $HAuCl_4$ (Sigma Aldrich), 38.8 mM sodium citrate (Sigma Aldrich).

In a 250 mL round-bottom flask equipped with a condenser, 150 mL of 1 mM $HAuCl_4$ was brought to a rolling boil with vigorous stirring (magnetic stir bar) in an oil bath. Rapid addition of 15 mL of 38.8 mM sodium citrate to the vortex of the solution resulted in a color change from pale yellow to burgundy. Boiling was continued for 10 min; the solution was removed from the oil bath, and stirring was continued for an additional 15 min. The solution was then allowed to reach room temperature prior to use.

Opal Synthesis:

The nanoparticle solution was then centrifuged, the solvent removed, and varying amounts of the remaining pellets were redispersed into a solution containing monodisperse colloidal suspension of particles (e.g., poly (methyl methacrylate) (PMMA) nanospheres (d~450 nm)) with a silica sol-gel (e.g., prepared from the acid-catalyzed hydrolysis of tetraethyl orthosilicate (TEOS)) prior to evaporative deposition of inverse opal photonic crystals onto a substrate. Thereafter, the colloidal template particles can be removed (e.g., by calcination for 8 h at 500° C.). The resulting porous inverse-opal photonic crystals generally have a face-centered-cubic geometry. Such a technique is described in PCT/US09/55044, which is incorporated by reference herein in its entirety.

Figure 22:
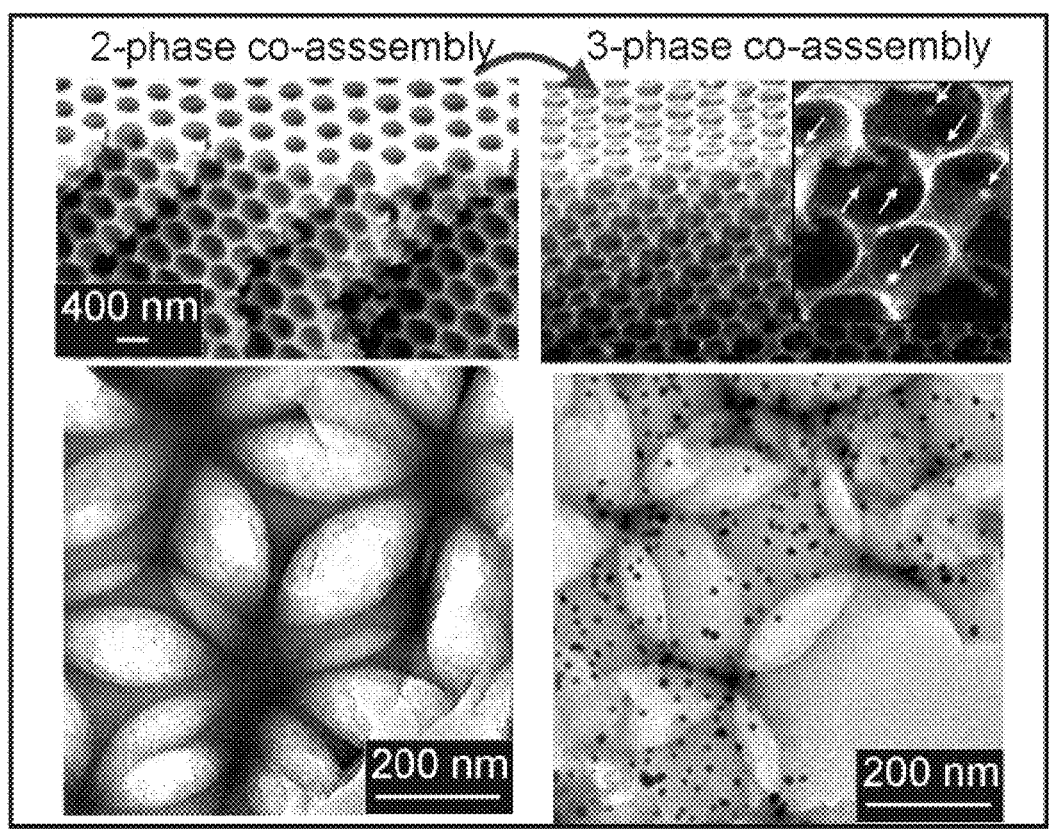
FIG. 22 shows SEM images of a photonic crystal fabricated with gold nanoparticles in accordance with certain embodiments.

FIG. 22 shows the SEM(top)/TEM(bottom) images comparing a photonic crystal produced using a 2-phase co-assembly on the left and 3-phase co-assembly on the right, where white arrows point out the gold nanoparticles in the SEM image, and the black dots represent the gold nanoparticles in the TEM image.

Figures 23A, 23B:
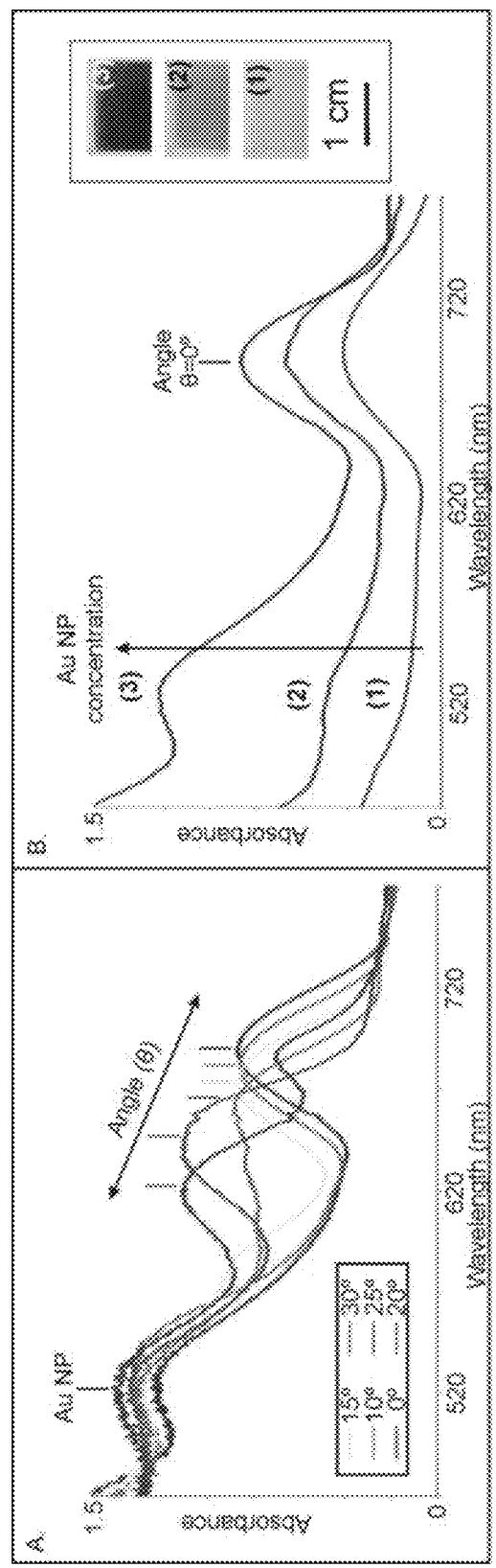
FIG. 23A-B shows absorbance spectra of photonic crystal containing gold nanoparticles in accordance with certain embodiments.

For the photonic crystals produced with the gold nanoparticles, FIG. 23A shows a peak arising from the plasmonic color effect of the gold nanoparticles at 520 nm as well as an angle-dependent color shift between 620-720 nm as a function of incident angle from the Bragg scattering. FIG. 23B shows that for an incident angle of 0°, the absorption peak near 520 nm increases as a function of increasing gold nanoparticle concentration (as added to colloid/silica solution prior to assembly) while there is no shift in the observed color at about 700 nm.

Figure 24:
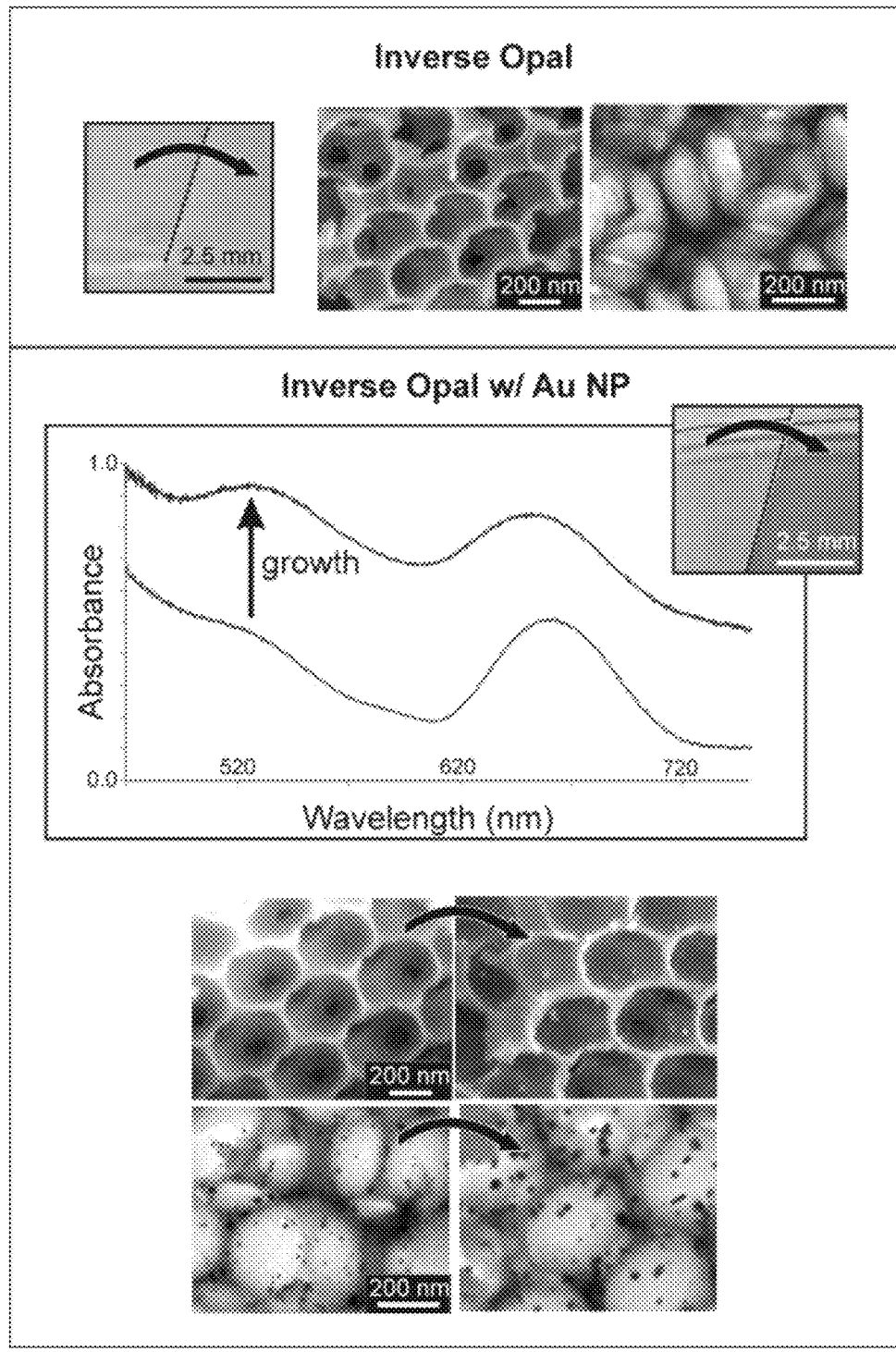
FIG. 24 shows SEM images and absorbance spectra of a photonic crystal containing gold particles before and after growth of the nanoparticles were carried out in accordance with certain embodiments.

FIG. 24 demonstrates that further growth of the nanoparticles can be carried out to further enhance the optical response (e.g., enhance color contrast). A gold nanoparticle growth solution that wets the photonic crystal was introduced. The opal was plasma-cleaned to provide hydrophilicity. The opal was immersed in a growth solution of dilute, aqueous hydroxylamine ($NH_2OH$) (Aldrich) and $HAuCl_4 \times 3H_2O$ (Aldrich). All glassware was thoroughly cleaned with aqua regia. The solution was stirred magnetically until the color of the photonic crystal began to visibly change (order of minutes). The growth solution leads to an increased nanoparticle size, as evident in the SEM image showing larger light spots (or dark spots in the TEM images). The absorbance spectrum shows an increase in the absorption peak attributed to the gold particles near 520 nm.

Figure 25:
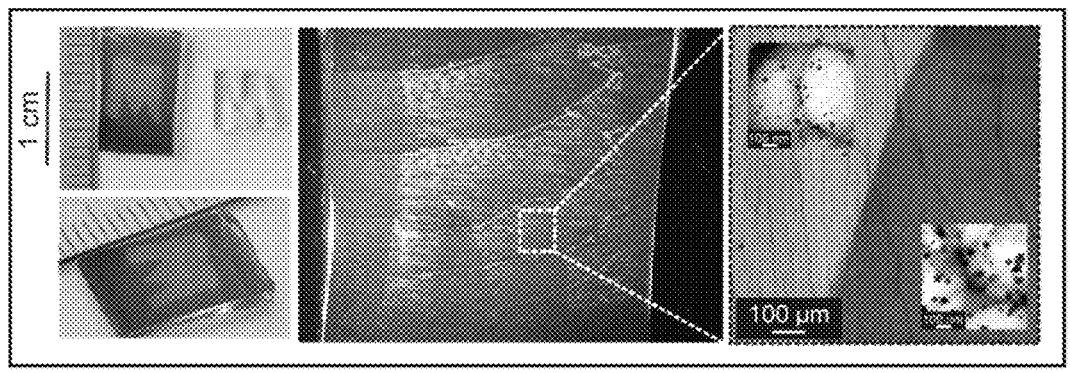
FIG. 25 shows images of a photonic crystal containing gold nanoparticles patterned with regions letter "M" showing different optical properties with different nanoparticle size in accordance with certain embodiments.

To demonstrate the selective growth of the nanoparticles to further enhance the optical response in only certain regions, a photonic crystal was patterned with a letter "M"

by exposing the regions outside of the letter "M" using oxygen plasma. The inverse opal was previously treated with a hydrophobic silane (tridecafluoro-1,1,2,2-tetrahydrooctyl)-trichlorosilane (Gelest Inc.) by vapor exposure in a desiccator under vacuum overnight. Then, a gold nanoparticle growth solution was introduced which wets only the hydrophilic portions of the photonic crystal. As shown in FIG. 25, the growth solution lead to an increased nanoparticle size in only the regions of the photonic crystals that are in contact with the growth solution (see lighter darker spots in SEM inset or darker spots in the TEM image). In contrast, the regions that are not in contact with the growth solution maintained the original nanoparticle size. Accordingly, the "M" shows an enhanced optical response as regions outside "M" were hydrophilic, were wetted by the growth solution, and the nanoparticles grew in the regions outside the "M" pattern.

Example 9

Figures 26A, 26B:
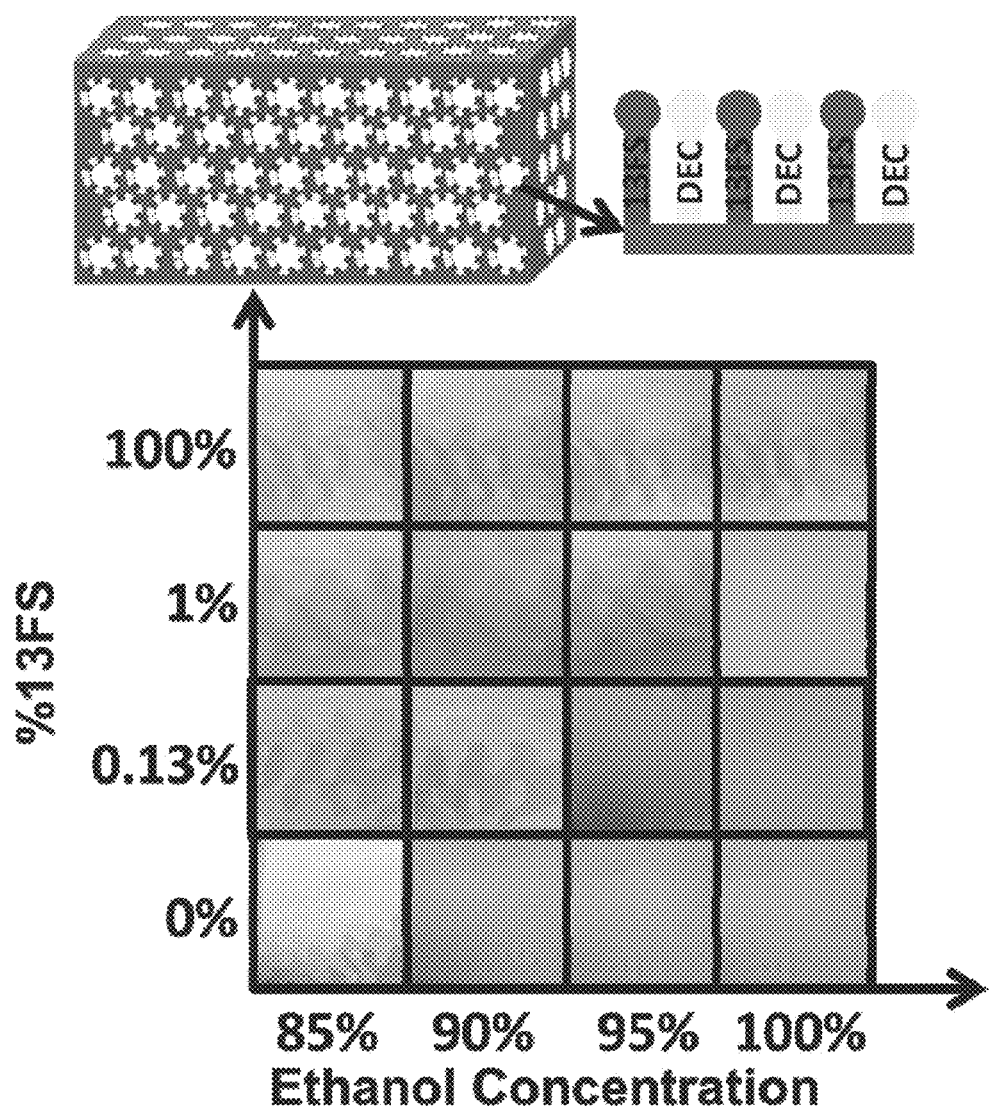
FIG. 26A-B shows selectivity of ethanol/water mixtures of photonic crystal based on different amounts of 13FS and DEC functional groups in accordance with certain embodiments.

Mixed 13FS:DEC monolayers were prepared by exposing photonic crystals to vapors from a liquid-liquid mixture of 13FS- and DEC-trichlorosilanes. As shown in FIG. 26A, adjusting the relative concentration of 13FS- and DEC-trichlorosilanes in the liquid-liquid mixture can alter the relative density of groups on the surface and was used to tune the infiltration threshold to occur at any ethanol concentration between 85% and 100%.

Ethanol-water mixtures of varying concentration was prepared to produce a continuum of surface tensions (and values of $\theta_c$). 13FS-functionalized photonic crystals display an unfilled state in all water-ethanol mixtures (including 100% EtOH) and DEC-functionalized photonic crystals display a filled state in EtOH concentrations larger than 85% (as enforced by quality control).

FIG. 26B is a response map showing four samples (each row is one photonic crystal) functionalized with 13FS, DEC and different mixtures of the two. Using mixtures of 13FS and DEC groups, photonic crystals whose wetting threshold occurs at 90% and 95% EtOH was achieved. By comparing the columns of the map shown in FIG. 26B, materials having such mixed functionalities can produce an array that colorimetrically identifies the relative concentration of a water-ethanol mixture to a precision of 5% across the full range selectivity offered by DEC and 13FS functionalities (85%-100% EtOH).

Example 10

Figure 27:
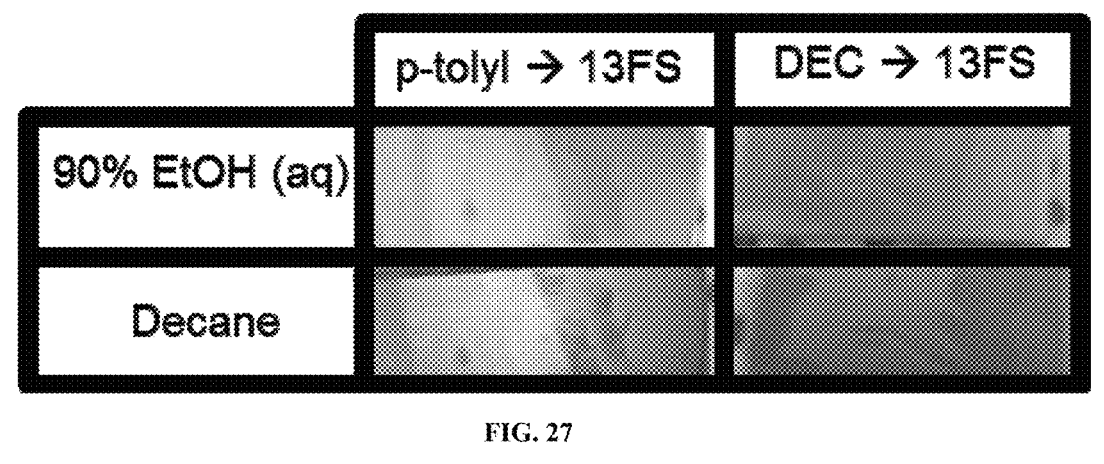

A photonic crystal having a vertical gradient of surface functionality that changes from p-tolyl to 13FS as a function of thickness was prepared. As shown in FIG. 27 (left column), n-decane and 90% ethanol in water (EtOH, (aq)) both induced the same colorimetric pattern. A second photonic crystal having a vertical gradient of surface functionality that changes from DEC to 13FS as a function of thickness was also prepared. As shown in FIG. 27 (right column), n-decane and 90% ethanol in water (EtOH, (aq)) exhibit different a different colorimetric response.

In other words, while the photonic crystal functionalized with a mixture of p-tolyl and 13FS sample can show the same pattern in 90% EtOH and n-decane (left column of FIG. 10), these liquids can show distinct patterns in a photonic crystal functionalized with a mixture of DEC and 13FS sample.

By building arrays of photonic crystals, each functionalized with different functional groups, it may be possible to extract even more specific information, by comparing the combinations of patterns produced by the array.

Example 11

For example, FIGS. 28A and 28B illustrate the effects of sample-to-sample variability in $\phi_0$ on the wetting outcomes for an inverse opal structure when the surface chemistry is fixed. As shown in the SEM images (bottom), the neck angles were estimated by measuring the ratio of the pore and neck widths (measured in the tangential direction), using $\sin(\phi_0) = r_{neck}/r_{pore}$. The mean neck angles measured from the images shown in FIGS. 28A and 28B are 24° and 17°, respectively. Both samples were functionalized with n-decylsilyl (DEC) groups (from exposure to vapors of the corresponding alkylchlorosilane). Photographs of both (top) show the two photonic crystals immersed in 85% (vol.) ethanol (EtOH) in water. The film in FIG. 28A, having a larger mean neck angle, is infiltrated by the liquid (discernable from the color), while the film in FIG. 28B, having the smaller mean neck angle, is not infiltrated. As shown, despite the same surface chemistries, the more easily-infiltrated photonic crystals is characterized by larger $\phi_0$.

Figure 29A:
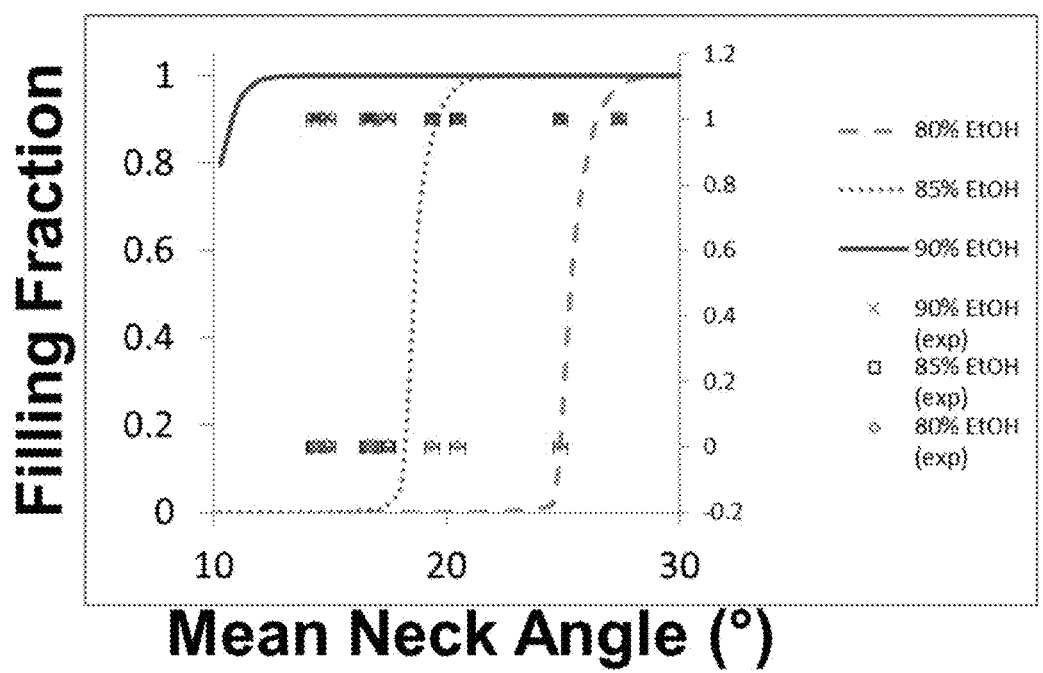
FIG. 29A demonstrates the filling fraction of different infiltrating liquids as a function of the average neck angles in inverse opal photonic crystals in accordance with certain embodiments.

Using intrinsic contact angles measured from DEC-functionalized flat surfaces, the expected equilibrium filling states were derived from bond connectivities using a numerical percolation simulation. The model considered an fcc lattice of pores, 30 close-packed layers thick with a large lateral area ($10^4$ unit cells). Neck-angles were randomly assigned to each nearest-neighbor connection according to a normal distribution. Inputting $\theta_c$ and starting with a completely filled top layer, the simulation filled all pores with paths of inter-pore fluid-connectivity (i.e. where $\phi_0 > \theta_c$) connecting them to the top filled layer. The solid curves in FIG. 29A show the simulated overall filling fraction for 90% ($\theta_c=13°\pm5°^{43}$), 85% ($\theta_c=22°\pm5°^{43}$), and 80% ($\theta_c=29°\pm5°^{43}$) EtOH for DEC-functionalized photonic crystals as a function of mean neck angle. A standard deviation of the mean neck angle of 3.2° was used in the simulations.

To verify the correlation between the neck angle and the wetting behavior, the neck angle distribution was characterized from SEM images sampled randomly across each film. The infiltration state from the presence or absence of iridescent color in 80%, 85% and 90% EtOH uniformly functionalized with DEC groups was also determined. These measurements are represented by the isolated points in FIG. 29A. As shown, FIG. 29A shows good agreement between the theoretical predictions and experimental results.

Short-range variability in the neck angles is what ultimately limits the selectivity of a photonic crystal's colorimetric response to liquids. Infiltration of a liquid through an photonic crystal with uniform surface chemistry and a random distribution of neck-angles will proceed as percolation through a regular fcc lattice with a bond-connectivity determined by $\theta_c$. The final equilibrated infiltration state will be a statistical distribution of filled and empty pores over a range of $\theta_c$ determined by the local variance of $\phi_0$. To extract a colorimetric selectivity from this continuous distribution of partial filling states, what constitutes "easily visually distinct" color patterns can be determined, which is inherently subjective. In this example, it was chosen to define easily visually distinct patterns as those with countable differences (e.g. each region can only be assigned two possible states). Therefore it was assumed that a user can only designate a region with uniform surface chemistry as being "unfilled" (bright color) and "filled" (transparent, negligible contrast with the underlying substrate).

A maximum fraction of filled pores that defines the colorimetric "unfilled" state and a maximum fraction of unfilled pores that defines the "filled" state was chosen in this example. The colorimetric selectivity (minimum resolvable difference in $\theta_c$) was defined by the range of $\theta_c$ over-which the filling fraction does not fit into either of these definitions. To extract this range, lower and upper bounds of connectivity were chosen to define the resolution limit of our colorimetric indicator. In estimating of the colorimetric selectivity, the bond percolation threshold that occurs at 12% connectivity for an fcc lattice was chosen as the upper-bound connectivity defining the "unfilled" state. For connectivity below the bond percolation threshold all paths of fluid flow have finite length. This means a sufficiently thick photonic crystal will have completely empty layers at equilibrium, thereby producing color that can be easily distinguished from the filled state.

Figure 29B:
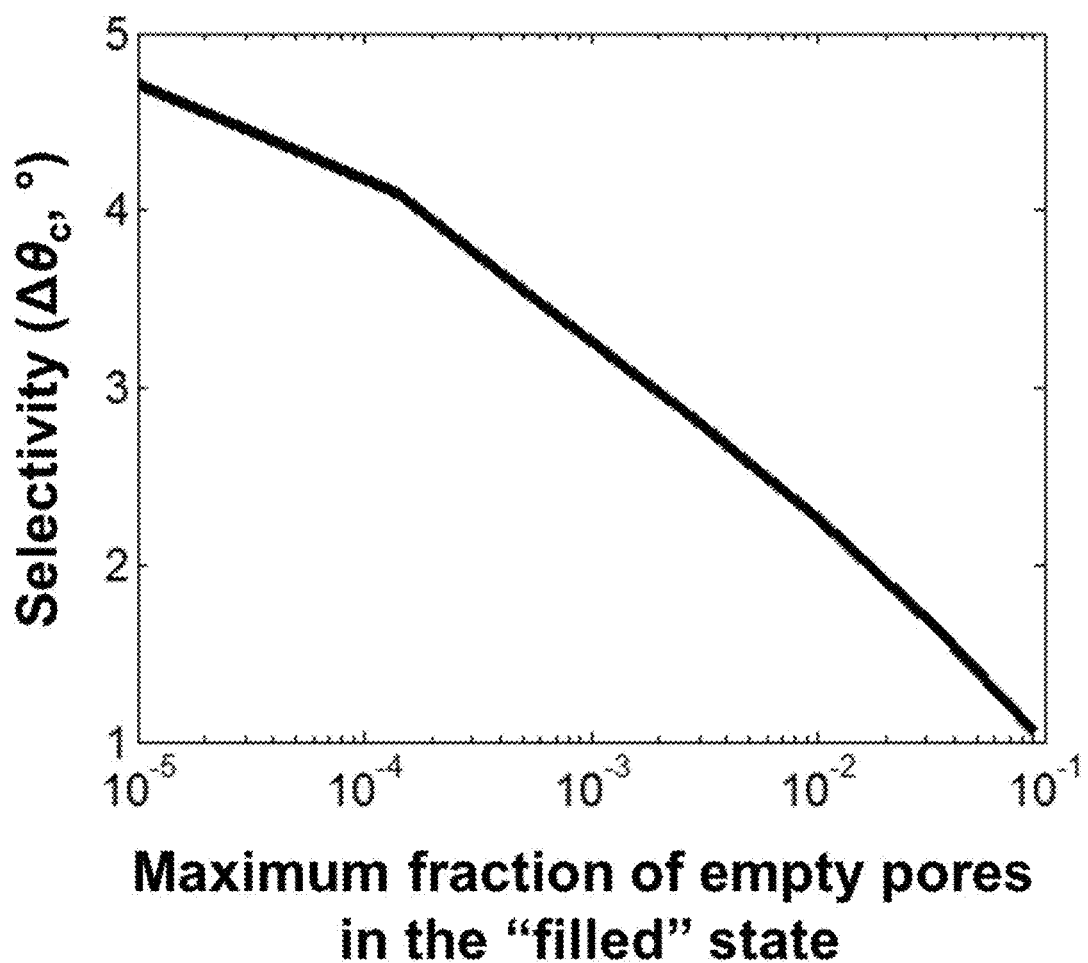
FIG. 29B shows a simulated plot of selectivity as a function of maximum fraction of empty pores in the filled state in accordance with certain embodiments.

The onset of the "filled" state was defined by a maximum tolerance of empty pores. FIG. 29B plots the selectivity (expressed in terms of $\theta_c$) as a function of this tolerance. The smallest tolerance shown in FIG. 29B ($10^5$ unit cells per unfilled pore) should be a very conservative estimate of this limit. $10^5$ unit cells per unfilled pore corresponds to an average distance of >30 μm (100 unit cells) between scattering centers and a fractional scattering cross-sectional area of $<10^{-4}$ for a film of typical thickness of 5 layers illuminated from above. Thus the scattered intensity from empty pores will be very low in this limit (the film appears transparent). Therefore a photonic crystal with uniform surface chemistry has the capacity to colorimetrically differentiate liquids based on differences in $\theta_c$ of less than 5°. This corresponds to concentration selectivity of at least 5% in water-ethanol mixtures.

Example 12

A photonic crystal was functionalized with the more lyophobic group ($R_1$, 13FS). Following a short (<2 min) exposure of the structure to oxygen plasma, some removal of the $R_1$ groups occurred, with the efficiency of removal decreasing with increasing depth. Subsequent addition of less lyophobic groups ($R_2$, DEC) via exposure to $SiCl_3R_2$ vapors generated a mixed, graded surface chemistry with an increasing ratio of $R_2/R_1$ from the bottom to the top of the photonic crystal.

Figure 30A:
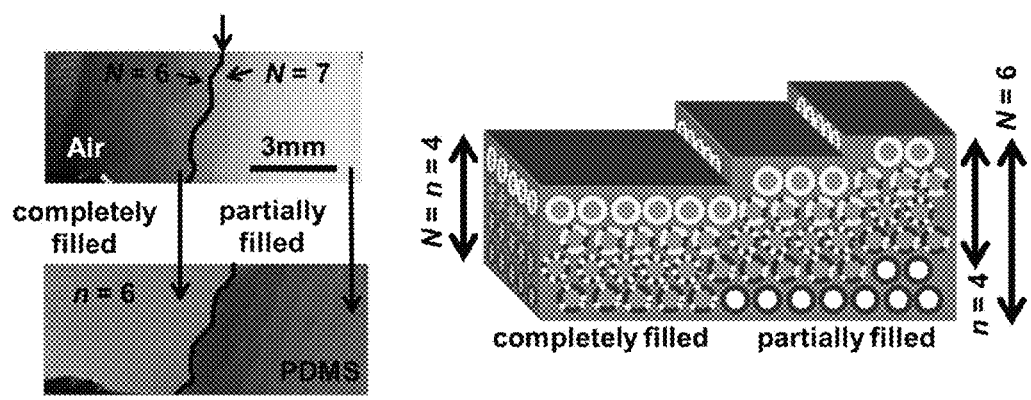
FIG. 30A shows images of photonic crystal having a vertical gradient of functional groups at different thicknesses that exhibits different optical properties depending on the depth of infiltration for the same infiltrating liquid in accordance with certain embodiments.

As a result, as illustrated in FIG. 30A, by varying the total thickness of the photonic crystal across the lateral dimensions, distinct depths of penetration can be viewed as distinct rainbow patterns whose size and location in the chip is unique to the depth filled.

Figure 30B:
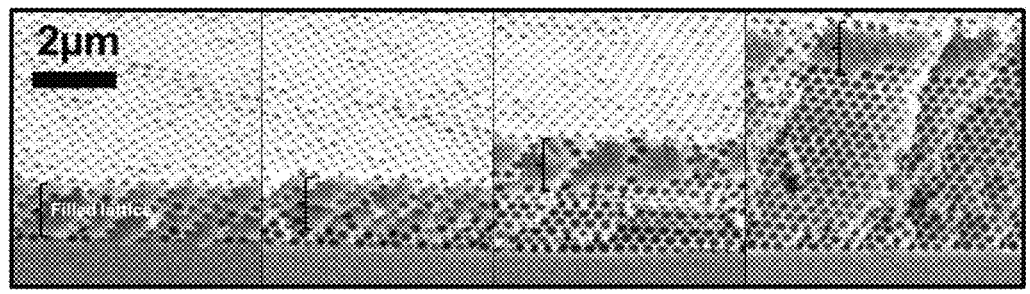
FIG. 30B shows SEM images of photonic crystal having a vertical gradient of functional groups having the same number of layers infiltrated by a liquid independent of the total thickness of the photonic crystal in accordance with certain embodiments.

The total thickness of the film varies from only two close-packed layers on the far left to a large number (>20 layers) on the far right, each visible "stripe" representing a region of fixed thickness, having one more layer than the stripe to the left of it. In thinner regions (N<~10) these stripes are wide enough to be visible by eye (~0.5-1 mm wide). In the thickest regions very close to the edges, the thickness increases on shorter length-scales and the stripes become harder to resolve. When this sample is immersed in liquid precursors to polydimethylsiloxane (PDMS, Sylgard 184, subsequently cured to allow visualization by SEM), the liquid completely penetrates the first 6 layers (n=6) and the photonic crystal becomes transparent (displaying the grey of the silicon substrate) in regions where N≤6. The SEM cross-sections in FIG. 30B shows the consistent penetration depth from the top of the photonic crystal, that is independent of the total thickness.

The color displayed by a photonic crystal having N layers, the top n-of-which are filled (n<N), should match the color produced by an empty (N-n)-layer photonic crystal, since the filled regions become transparent, provided there is sufficient index-matching between the fluid and the silica. FIG. 31A shows four segments of photonic crystal, all functionalized with a DEC→13FS (DEC on top and 13FS on bottom) vertical gradient using different plasma-exposure-times and immersed in PDMS precursors (subsequently cured). Owing to the varied oxygen plasma exposure time, the PDMS completely filled the lattice up to a different depth in each sample. However, as illustrated by the normalized reflectance spectra in FIGS. 31B to 31D, the apparent color in a given region depends only on the number of unfilled layers (N-n) and is relatively insensitive to the total thickness (N).

Figure 32A:
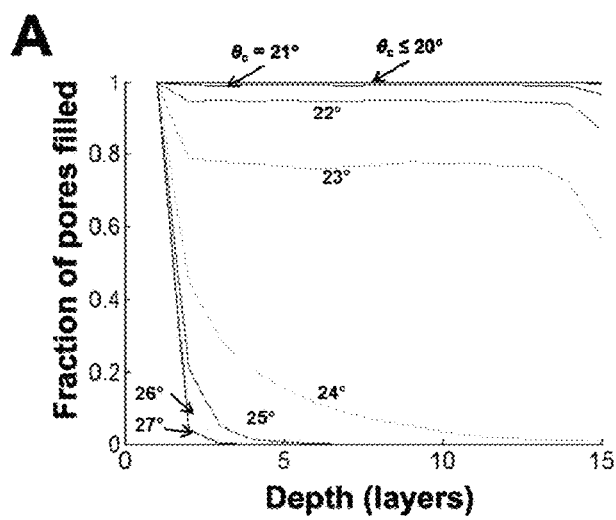
FIGS. 32A and B shows plot of fraction of pores filled as a function of depth for a photonic crystal having uniform functionality and a photonic crystal having a vertical gradient of functionality, respectively, in accordance with certain embodiments.
Figure 32B:
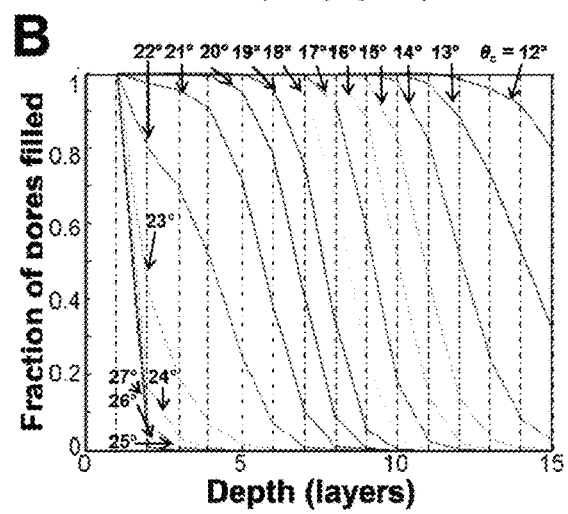
FIG. 32C shows images of different "teeths" of photonic crystals having a vertical gradient of functional groups to demonstrate an improved sensitivity to the detectable selectivity of infiltrating liquid relative to a photonic crystal having uniform functionality in accordance with certain embodiments.

FIGS. 32A and 32B show two percolation simulations (using 15-layer photonic crystals) comparing photonic crystals with uniform and graded surface chemistry that illustrate this effect. FIG. 32A shows the filling fraction as a function of the depth in a photonic crystal ($<\phi_0>=19.6°$, $SD(\phi_0)=3°$) with spatially homogeneous surface chemistry for liquids with all integer $\theta_c$ values over the range [12°-27°]. As shown, partial wetting in uniformly-functionalized photonic crystal takes on two qualitative forms. For $\theta_c$ higher than the percolation threshold ($\theta_c>23°$ for this photonic crystal), the filling fraction decays exponentially with depth. These filling profiles can be colorimetrically identified as "unfilled" because regions of sufficiently large total thickness will contain completely unfilled layers. For $\theta_c$ lower than the percolation threshold ($\theta_c\leq23°$ in FIG. 32A), the filling fraction is roughly homogeneous throughout the structure.

In contrast, FIG. 32B shows simulated infiltration profiles for the same photonic crystal structure with $\theta_c$ increasing with depth, but having a vertically patterned functionalization. To approximate the type of gradation that might be produced, $\theta_c$ was allowed to obey a cumulative normal distribution (mean=7 layers, SD=3 layers) as a function of depth, having the same values as FIG. 32A (shown for each curve in FIG. 32B) at the top layer, but increasing with depth by a total magnitude of 10° over 15 layers (12°-27° at layer 1, 22°-37° at layer 15). As shown, most (e.g. $\theta_c=13°-21°$ display the same filling profile, but successive curves are shifted by one or more layers.

Accordingly, if the filling liquid has a similar refractive index as the photonic crystal, adjacent curves in FIG. 32B would appear as identical "rainbow" patterns, shifted in space by one layer-step in a photonic crystal having a varying total-thickness. These patterns could be easily visually differentiable at any angle by measuring the distance (or counting the number of layer steps) to the start of the "rainbow" pattern.

Figure 32C:
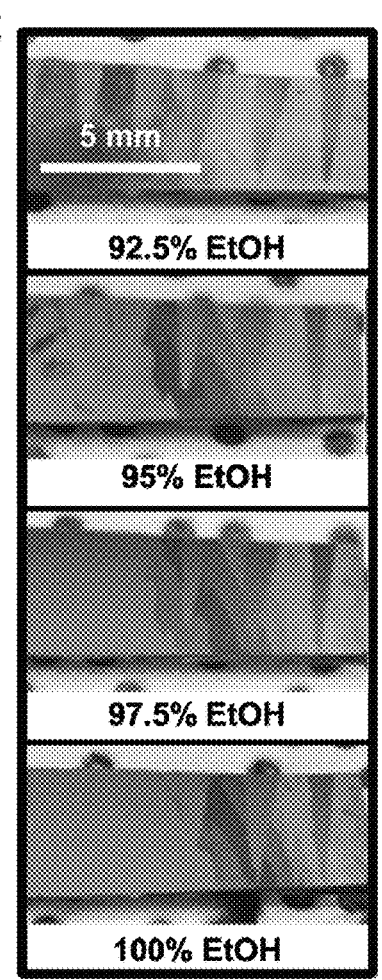

FIG. 32C shows a DEC→13FS (45 s etch time) vertical gradient in which 92.5% EtOH, 95% EtOH, 97.5% EtOH and 100% EtOH are distinguished colorimetrically. In this sample, a 2.5% increase in ethanol concentration is sufficient to increase the final filling depth by enough to produce a clearly different visual pattern. To enhance the visualization of these distinct wetting profiles, we can selectively mask only certain regions of the final functionalized photonic crystals (which in this example has a laterally uniform DEC→13FS vertical gradient and a spatially varying total thickness) and apply a final oxygen plasma oxidation to effectively remove certain regions from the colorimetric readout (i.e. these regions become wetting to all liquids). Alternatively, this can be done by selectively removing the photonic crystal in these regions, either physically (i.e. by scratching) or chemically (i.e. by etching with focused ion beam, reactive ion etching etc.). In the example shown in FIG. 32C, an array of hydrophilic "teeth" have been defined via selective oxidation to aid in the visualization (i.e. increase the countability).

In certain embodiments, in order to further enhance the visual perceptibility certain regions of the photonic crystal can be selectively oxidized to control the patterns that appear in the different analyte liquids. FIG. 33 shows four examples of indicator strips using both homogeneously mixed monolayers (FIG. 33A) and vertical gradients of wettability (FIGS. 33B-D), where this extra step of selective oxidation has been incorporated to enhance the readability of the strips.

FIGS. 33A and 33B both show indicators that mutually distinguish methanol ($\gamma=22.1$ mN/m), ethanol ($\gamma=21.8$ mN/m) and isopropanol ($\gamma=20.9$ mN/m). The sample in FIG. 33A consists of two chips, held together: on the left, the letter "M" has been defined in a photonic crystal that is functionalized with 1% 13FS (99% DEC); on the right, the letter "E" has been functionalized with 16.7% 13FS. When the two are submerged together, they read "ME" for methanol, "E" for ethanol and appear blank in isopropanol.

In FIG. 33B, the same alcohols are distinguished in photonic crystal that has been functionalized with a vertical gradient, where the functional groups change from DEC to 13FS (DEC→13FS) with increasing depth. In this sample, the photonic crystal's thickness increases from the left to the right. To enhance the readability of patterns produced by vertical gradients, the functionalized regions were patterned into an array of "teeth" by selectively oxidizing the areas around the "teeth." This patterning reduces a "measuring" problem to a "counting" problem, which is easier to do roughly by eye (i.e. without a ruler). Methanol, ethanol, and isopropanol are distinguished simply by counting the number of "teeth" visible. As each "tooth" contains only two or three layer steps, a change in penetration depth of ~1 layer (e.g. ethanol vs. isopropanol) induces the disappearance of a large fraction of the third tooth from the left.

FIG. 33C shows the same strategy applied to differentiating aliphatic compounds. Distinct "teeth" profiles are viewed in hexane ($\gamma=18.6$ mN/m), heptane ($\gamma=19.9$ mN/m), octane ($\gamma=21.4$ mN/m), nonane ($\gamma=22.6$ mN/m), and decane ($\gamma=23.6$ mN/m).

FIG. 33D illustrates how regions of uniform functionality and vertical gradient can be combined in the same photonic crystal. The photonic crystal is patterned with two stripes on an oxidized (ROH) background. The rightmost strip is functionalized with 13FS while the leftmost stripe is comprised of a vertical gradient, where the functional groups change from DEC to 13FS (DEC→13FS) with increasing depth. This is accomplished by masking the left half of the photonic crystal during the short oxygen-plasma step. The sample displays one stripe when immersed in regular unleaded gasoline and two stripes when immersed in diesel. These examples illustrate how a final oxidation step can enhance the user-friendliness. Through the use of a small legend sheet accompanying the chip, users could compare patterns or simply count the number of visible bars to quickly and reliably differentiate the set of liquids for which a given photonic crystal has been optimized.

What is claimed is:

1. A system for providing an indication of the presence of one or more indicator materials, the system comprising:
   a porous three-dimensional photonic structure comprising a first region and a second region;
   wherein said first region comprises a first functional group on at least some of the interior surfaces of the porous three-dimensional photonic structure to provide a first surface property;
   wherein said second region comprises a second functional group on at least some of the interior surfaces of the porous three-dimensional photonic structure to provide a second surface property;
   wherein the first functional group interacts with a first indicator material differently than the second functional group; and
   wherein a spatial gradient of surface properties are present between said first region and said second region such that the surface properties gradually change from said first region to said second region.

2. The system of claim 1, wherein the said first region and the second region are located apart from each other in a lateral dimension of the photonic structure.

3. The system of claim 1, wherein the first region and the second region are located apart from each other in a vertical dimension of the photonic structure.

4. The system of claim 1, wherein the thickness of the porous three-dimensional photonic structure in the first region is greater than the thickness of the porous three-dimensional photonic structure in the second region.

5. The system of claim 1, wherein said first indicator material is a fluid.

6. The system of claim 1, wherein said first region and second region have a substantially similar visible appearance in the absence of said first indicator material.

7. The system of claim 4, wherein said first indicator material fills at least some of the pores of said first region, and said first region has a different reflectance spectrum than the reflectance spectrum of said second region.

8. The system of claim 1, wherein the first surface property includes wettability, hydrophobicity, hydrophilicity, lyophobicity, or lyophilicity.

9. The system of claim 1, wherein the first functional group interacts with a second indicator material differently than the second functional group.

10. The system of claim 1, further comprising a third region which comprises a third functional group on at least some of the interior surface of the porous three-dimensional photonic structure.

11. The system of claim 1, wherein said first region comprises a first functional group present on substantially all of the interior surfaces of said first region.

12. The system of claim 11, wherein said first functional group includes reactive groups, protecting groups, hydrophilic groups, hydrophobic groups, lyophilic groups, lyophobic groups, nanoparticles or mixtures thereof.

13. The system of claim 1, wherein the porous three-dimensional photonic structure is an inverse opal structure, a mesoporous silica, a short range order structure exhibiting structural color, a quasicrystal, or mixtures thereof.

14. The system of claim 1, wherein the first region and said second region are patterned to provide an encrypted message that is readily visible after the first indicator material occupies at least some of the pores of said first region.

15. The system of claim 1, wherein the first region is capable of wicking up said first indicator material.

16. The system of claim 1, wherein the first region and the second region are located apart from each other in a lateral dimension of the photonic structure.

17. The system of claim 1, wherein the pore sizes are selected to provide a predetermined energy barrier for the first indicator material to infiltrate at least some of the pores of said first region.

18. The system of claim 1, further comprising one or more additives within the photonic structure to enhance optical response of the photonic structure.

19. The system of claim 1, wherein the first indicator material comprises oil or a chemical reagent.

20. The system of claim 1, wherein the first functional group comprises reactive functional groups.

21. The system of claim 1, further comprising a third region, said third region comprising a third functional group on at least some of the interior surfaces of the porous three-dimensional photonic structure to provide a third surface property.

22. The system of claim 21, further comprising a second spatial gradient of surface properties between said second region and said third region such that the surface properties gradually change from said second region to said third region.

23. The system of claim 1, wherein the system is a sensor.

24. A method comprising:
providing a porous three-dimensional photonic structure; and
patterning said porous three-dimensional photonic structure to provide a first region and a second region,
wherein said first region comprises a first functional group on at least some of the interior surfaces of the porous three-dimensional photonic structure to provide a first surface property;
wherein said second region comprises a second functional group on at least some of the interior surfaces of the porous three-dimensional photonic structure to provide a second surface property;
wherein the first functional group interacts with a first indicator material differently than the second functional group; and
wherein a spatial gradient of surface properties are present between said first region and said second region such that the surface properties gradually change from said first region to said second region.

25. The method of claim 24, further comprising:
providing a mask in or over at least said second region of said porous three-dimensional photonic structure.

26. The method of claim 24, wherein said first region comprises a first functional group present on substantially all of the interior surfaces of said first region.

27. The method of claim 24, wherein said first functional group includes reactive groups, protecting groups, hydrophilic groups, hydrophobic groups, lyophilic groups, lyophobic groups, nanoparticles or mixtures thereof.

28. The method of claim 27, further comprising:
providing said first region of said porous three-dimensional photonic structure with a reagent that reacts with said first functional group.

29. The method of claim 24, further comprising:
providing said first indicator material that selectively fills at least some of the pores of said first region.

30. The method of claim 29, where said first indicator material wicks into at least some of the pores of the first region.

31. The method of claim 24, wherein said first region is patterned to provide an encrypted message that is not visible until the first indicator material occupies at least some of the pores of said first region.

32. The method of claim 24, wherein the porous three-dimensional photonic structure is an inverse opal structure, a mesoporous silica, a short range order structure exhibiting structural color, a quasicrystal, or mixtures thereof.

33. The method of claim 24, wherein the first region and the second region are located apart from each other in a lateral dimension of the photonic structure.

34. The method of claim 24, wherein the first region and the second region are located apart from each other in a vertical dimension of the photonic structure.

35. The method of claim 24, wherein the pore sizes are selected to provide a predetermined energy barrier for the first indicator material to infiltrate at least some of the pores of said first region.

36. The method of claim 24, further comprising introducing one or more additives within the photonic structure to enhance optical response of the photonic structure.

37. The method of claim 24, wherein the first indicator material is a fluid.

38. The method of claim 24, wherein the first indicator material comprises oil or a chemical reagent.

39. The method of claim 24, further comprising:
patterning said porous three-dimensional photonic structure to provide a third region,
wherein said third region comprises a third functional group on at least some of the interior surfaces of the porous three-dimensional photonic structure to provide a third surface property.

40. The method of claim 39, wherein a spatial gradient of surface properties are present between said second region and said third region such that the surface properties gradually change from said second region to said third region.

* * * * *